US005962246A

United States Patent [19]
Ladner et al.

[11] Patent Number: 5,962,246
[45] Date of Patent: Oct. 5, 1999

[54] DUTPASE, ITS ISOFORMS, AND DIAGNOSTIC AND OTHER USES

[75] Inventors: Robert D. Ladner, Haddonfield; Frank Lynch, Marlton; Salvatore J. Caradonna, Voorhees, all of N.J.

[73] Assignee: The University of Medicine and Dentistry of New Jersey, Piscataway, N.J.

[21] Appl. No.: 08/824,405

[22] Filed: Mar. 26, 1997

Related U.S. Application Data

[60] Provisional application No. 60/014,748, Mar. 29, 1996.

[51] Int. Cl.$^6$ ............................. C12Q 1/42; C12Q 1/00; C12N 9/14; C12N 9/16
[52] U.S. Cl. ................................. 435/21; 435/4; 435/18; 435/195; 435/196
[58] Field of Search ................................. 435/195, 4, 18, 435/21, 196

[56] References Cited

U.S. PATENT DOCUMENTS 5,264,343  11/1993  Krystosek et al. ........................... 435/6

OTHER PUBLICATIONS

Wist, Partial Purification of Deoxyuridine Triphosphate Nucleotidohydrolase And Its Effect on DNA Synthesis in Isolated HeLa Cell Nuclei, *Biochimica et Biophysica Acta.* 565:98–106, 1979.

Duker and Grant, Alterations in the levels of deoxyuridine triphosphatase, uracile–DNA glycosylase and AP endonuclease during the cell cycle, *Exp Cell Res.* 125: 493–497, 1980.

Caradonna and Adamkiewicz, Purification and Properties of the Deoxyuridine Triphoshate Nucleotidohydrolase Enzyme Derived from HeLa S3 Cells, *The Journal of Biological Chemistry* 259:5459–5464, 1984.

Brown and Gatter, Monoclonal antibody Ki–67: its use in histopathology, *Histophology* 17: 489–503, 1990.

Lirette and Caradonna, Inhibition of Phosphorylation of Cellular dUTP Nucleotidohydrolase as a Consequence of Herpes Simplex Virus Infection, *Journal of Cellular Biochemistry* 43: 339–353, 1990.

Horikoshi et al., Quantitation of Thymidylate Synthase, Dihydrofolate Reducatese, and DT–Diaphorase Gene Expression in Human Tumors Using the Polymerase Chain Reaction, *Cancer Research* 52: 108–116, 1992.

McIntosh et al., Human dUTP pyrophosphatase cDNA sequence and potential biological importance of the enzyme, *Pro. Natl. Acad. Sci. USA* 89: 8020–8024, 1992.

Muller and Caradonna, Cell Cycle Regulation of a Humann Cyclin–like Gene Encoding Uracile–DNA Glycosylase, *The Journal of Biological Chemistry* 268: 1310–1319, 1993.

Hall, Assessment of Cell Proliferation Markers with Particular Emphasis on Ki–67 and PCNA, *Report for DAKO A/S*, 1993.

Strahler et al., Maturation stage and proliferation–dependent expression of dUTPase in human T cells, *Proc. Natl. Acad. Sci. USA* 90: 4991–4995, 1993.

Canman et al., Resistance to Fluorodeoxyuridine–induced DNA Damaged and Cytotoxicity Correlates with an Elevation of Deoxyuridine Triphosphatase Activity and Failure to Accumulate Deoxyuridine Triphosphate, *Cancer Research* 53: 5219–5224, 1993.

Climie et al., Expression of Trimeric Human dUTP Pyrophosphatase in *Escherichia coli* and Purification of the Enzyme, *Protein Expression and Purification* 5: 252–258, 1994.

Canman et al., Induction of Resistance to Fluorodeoxyuridine Cytotoxicity and DNA Damage in Human Tumor Cells by Expression of *Escherichia coli* Deoxyuridinetriphosphatase, *Cancer Research* _:2296–2298, 1994.

Ladner and Caradonna, *Proceedings of the Americna Association For Cancer Research* vol. 35, Abstract 3200, 1994.

Ladner and Caradonna, *Proceedings of the Americna Association For Cancer Research* vol. 35, Abstract 3022, 1994.

Johnston, et al., Thymidylate Synthase Gene and Protein Expression Correlate and Are Associated with Response to 5–Fluorouracil in Human Colorectal and Gastric Tumors, *Cancer Research* 55: 1407–1412, 1995.

Lander et al., Characterization of Distinct Nuclear and Mitochondrial Forms of Human Deoxyuridine Triphospate Nucleotidohydrolase, *The Journal of Biological Chemistry* 271: 7745–7751, 1996.

Ladner et al., Identification of a Consensuus Cyclin–dependent Kinase Phosphorylation Site Unique to the Nuclear form of Human Deoxyuridine Triphosphate Nucleotidohydrolase, *The Journal of Biological Chemistry* 271: 7752–7757, 1996.

Mol et al., Human dUTP pyrophosphatase: uracile recognition by a β hairpin and active sites formed by three separate subunits, *Structure* 4: 1077–1092, 1996.

Ladner and Caradonna, The Human DUTPase Gene Encodes both Nuclear and Mitochondrial Isoforms, *The Journal of Biological Chemistry* 272: 19072–19080, 1997.

Cohen et al., Assignment of the Human dUTPase Gene (DUT) to Chromosome 15q15–q21.1 by Fluoroescence in Situ Hybridization, *Genomics* 40: 213–215, 1997.

dUTPase as a target for drug discovery, Allelix Press Release, 1994.

*Primary Examiner*—Robert A. Wax
*Assistant Examiner*—Einar Stole
*Attorney, Agent, or Firm*—Dechert Price & Rhoads

[57] ABSTRACT

The invention provides the DNA and amino acid sequence of dUTPase, an enzyme which is essential for life and which is increased during periods of cellular proliferation. The human form of the dUTPase enzyme has been found to have two isoforms, a nuclear and a mitochondrial isoform. Methods of determining the proliferation status of a cell, efficacy of antineoplastic compounds, and response to therapy with antineoplastic compounds, using cellular levels of dUTPase is disclosed. A kit containing the necessary reagents for the determination of dUTPase is also disclosed.

14 Claims, 21 Drawing Sheets

```
                                            CGTCTCCTCGCTCGCCTTCTGGCTCTGCC

M   P   C   S   E   E   T   P   A   I   S   P   S   K   R   A
ATG CCC TGC TCT GAA GAG ACA CCC GCC ATT TCA CCC AGT AAG CGG GCC

R   P   A   E   V   G   G   M   Q   L   R   F   A   R   L   S
CGG CCT GCG GAG GTG GGC GGC ATG CAG CTC CGC TTT GCC CGG CTC TCC

E   H   A   T   A   P   T   R   G   S   A   R   A   A   G   Y
GAG CAC GCC ACG GCC CCC ACC CGG GGC TCC GCG CGC GCC GCG GGC TAC

D   L   Y   S   A   Y   D   Y   T   I   P   P   M   E   K   A
GAC CTG TAC AGT GCC TAT GAT TAC ACA ATA CCA CCT ATG GAG AAA GCT

V   V   K   T   D   I   Q   I   A   L   P   S   G   C   Y   G
GTT GTG AAA ACG GAC ATT CAG ATA GCG CTC CCT TCT GGG TGT TAT GGA

R   V   A   P   R   S   G   L   A   A   K   H   F   I   D   V
AGA GTG GCT CCA CGG TCA GGC TTG GCT GCA AAA CAC TTT ATT GAT GTA

G   A   G   V   I   D   E   D   Y   R   G   N   V   G   V   V
GGA GCT GGT GTC ATA GAT GAA GAT TAT AGA GGA AAT GTT GGT GTT GTA

L   F   N   F   G   K   E   K   F   E   V   K   K   G   D   R
CTG TTT AAT TTT GGC AAA GAA AAG TTT GAA GTC AAA AAA GGT GAT CGA

I   A   Q   L   I   C   E   R   I   F   Y   P   E   I   E   E
ATT GCA CAG CTC ATT TGC GAA CGG ATT TTT TAT CCA GAA ATA GAA GAA

V   Q   A   L   D   D   T   E   R   G   S   G   G   F   G   S
GTT CAA GCC TTG GAT GAC ACC GAA AGG GGT TCA GGA GGT TTT GGT TCC

T   G   K   N   *  [SEQ ID NO:2]
ACT GGA AAG AAT TAA AATTTATGCCAAGAACAGAAAACAAGAAGTCATACCTTTTTCT
TAAAAAAAAAAAAAGTTTTTGCTTCAAGTGTTTTGGTGTTTTGCACTTCTGTAAACTTACTAG
CTTTACCTTCTAAAAGTACTGCATTTTTTACTTTTTTTTATGATCAAGGAAAAGATCATTAAA
AAAAAACACAAAAGAAGTTTTTCTTTGTGTTTGGATCAAAAAGAAACTTTGTTTTTCCGCAAT
TGAAGGTTGTATGTAAATCTGCTTTGTGGTGACCTGATGTAAACAGTGTCTTCTTAAAATCAA
ATGTAAATCAATTACAGATTAAAAAAAAAAGCCTGTATTTAACTCATATGATCTCCCTTCAG
CAACTTATTTTGCTTTAATTGCTTTAAATCTTAAGCAATATTTTTATTCAGTAAACAAATTC
TTTCACAAGGTACAAAATCTTGCATAAGCTGAACTAAAATAAAAATGAAAAGGAGAGATTAAA
AAAAAAAAAAAAAAAAAAAAAAAAAAA [SEQ ID NO:1]
```

FIG. 1

GGTGGAAGCCTGGCGCACGTCCGGAGGTGCCGAGGACCCAACCAGCCCAAACTCTGGGGGAA

```
  M   T   P   L   C   P   R   P   A   L   C   Y   H   F   L   T
 ATG ACT CCC CTC TGC CCT CGC CCC GCG CTC TGC TAC CAT TTC CTT ACG

S   L   L   R   S   A   M   Q   N   A   R   G   T   A   E   G
 TCT CTG CTT CGC TCA GCG ATG CAA AAC GCG CGA GGC ACG GCA GAG GGC

R   S   R   G   T   L   R   A   R   P   A   P   R   P   P   A
 CGA AGC CGC GGT ACT CTC CGG GCC AGG CCC GCC CCT CGG CCG CCG GCG

A   Q   H   G   I   P   R   P   L   S   S   A   G   R   L   S
 GCG CAG CAC GGG ATT CCC CGG CCG CTG TCC AGC GCT GGC CGC CTG AGC

Q   G   C   R   G   A   S   T   V   G   A   A   G   W   K   G
 CAA GGC TGC CGC GGA GCC AGT ACA GTC GGG GCC GCT GGC TGG AAG GGC

E   L   P   K   A   G   G   S   P   A   P   G   P   E   T   P
 GAG CTT CCT AAG GCG GGG GGA AGC CCG GCG CCG GGG CCG GAG ACA CCC

A   I   S   P   S   K   R   A   R   P   A   E   V   G   G   M
 GCC ATT TCA CCC AGT AAG CGG GCC CGG CCT GCG GAG GTG GGC GGC ATG

Q   L   R   F   A   R   L   S   E   H   A   T   A   P   T   R
 CAG CTC CGC TTT GCC CGG CTC TCC GAG CAC GCC ACG GCC CCC ACC CGG

G   S   A   R   A   A   G   Y   D   L   Y   S   A   Y   D   Y
 GGC TCC GCG CGC GCC GCG GGC TAC GAC CTG TAC AGT GCC TAT GAT TAC

T   I   P   P   M   E   K   A   V   V   K   T   D   I   Q   I
 ACA ATA CCA CCT ATG GAG AAA GCT GTT GTG AAA ACG GAC ATT CAG ATA

A   L   P   S   G   C   Y   G   R   V   A   P   R   S   G   L
 GCG CTC CCT TCT GGG TGT TAT GGA AGA GTG GCT CCA CGG TCA GGC TTG

A   A   K   H   F   I   D   V   G   A   G   V   I   D   E   D
 GCT GCA AAA CAC TTT ATT GAT GTA GGA GCT GGT GTC ATA GAT GAA GAT

Y   R   G   N   V   G   V   V   L   F   N   F   G   K   E   K
 TAT AGA GGA AAT GTT GGT GTT GTA CTG TTT AAT TTT GGC AAA GAA AAG

F   E   V   K   K   G   D   R   I   A   Q   L   I   C   E   R
 TTT GAA GTC AAA AAA GGT GAT CGA ATT GCA CAG CTC ATT TGC GAA CGG

I   F   Y   P   E   I   E   E   V   Q   A   L   D   D   T   E
 ATT TTT TAT CCA GAA ATA GAA GAA GTT CAA GCC TTG GAT GAC ACC GAA

R   G   S   G   G   F   G   S   T   K   N   *[SEQ ID NO:4]
 AGG GGT TCA GGA GGT TTT GGT TCC ACT GGA AAG AAT TAA AATTTATGCCA
```

AGAACAGAAAACAAGAAGTCATACCTTTTTCTTAAAAAAAAAAAAAGTTTTTGCTTCAAGTGT
TTTGGTGTTTTGCACTTCTGTAAACTTACTAGCTTTACCTTCTAAAAGTACTGCATTTTTTAC
TT [SEQ ID NO:3]

FIG. 2

GATCCTCTAGAGTCGACCTGCAGGTCGACTCTAGAGGATCCTTGTTCGACTCCTAGCAAGGGGTT

CCCACTGCGTTTCTGTTGGGTTATCCCAAACCTCTGATAGGATAGTAGCGCCCTCCCTGCCTCCG

GTCGAATAAACACTACAACGTCTGACACTCGGTGCTGAAAGGAAATCGGGCGCAATAACTGTCAC

CGGCGCCGAGATGCGGTTCGGCGCTTAGGCCTAAACTCAGAGCCCGGGAGTCATGGCTGCCGGGG

TGCCGCCCCAGGTAAATCAGTCCAGGCGCAGGGCCCGGGCCTGGCGTACACTCTCGGAAAAATGG

GGGCCAGAGCAAACAAGAAGAGCGAAAGCAAGAGGGCTAGGCAGCCAGAGGGCAGAAGACTCAAG

ACGCCAACGGCCGTCTTCCTGGGGCCCCAGGGCTGCGCCATCCCTGGGCTGCCGGGGCACCGCCT

CTCCACGCCCCTCGTCCGGCGGCGGCTGCGACTGCTTCCGAGGTCATGTTCCCAGGACGGGCGCG

TCTTCAGGGTGGAAGCCTGGCGCACGTCCGGAGGTGCCGAGGACCCAACCAGCCCAAACTCTGGG
      ↘ DUT-M

GGAAATGACTCCCCTCTGCCCTCGCCCCGCGCTCTGCTACCATTTCCTTACGTCTCTGCTTCGCT

CAGCGATGCAAAACGCGCGAGGCACGGCAGAGGGCCGAAGCCGCGGTACTCTCCGGGCCAGGCCC

GCCCCTCGGCCGCCGGCGGCGCAGCAC<u>GGGATTCCCC</u>GGCCGCTGTCCAGCGCTGGCCGCCTGAG
                                     NFκB

CCAAGGCTGCCGCGGAGCCAGTACAGTCGGGGCCGCTGGCTGGAAGGGCGAGCTTCCTAAGGCGG

GGGGAAGCCCGGCGCCGGGGCCGGGTAGGAAAGGCGGGGGAGGGGCTCCGGCCGTCTGGAAGGAA

TCCACGCGGCTTGAGGCTGTGGGGAAGTAGGGTGGCGAGCGGTGGTTCTGCGCGCGGGGGGCGGG

GGGGTGGGGTGGTCCATTAGGGGCCCCTGGCGAGGGGCGGCTTTCTAGTGTGTGAGGCGACGCC

CTAGAAGCTCCCCTTCAAAGTTGGCCCCACGCGCTGAATGTGGAAAGTTGACTGGGACCCAGTAG

TTTCCCATCCCAAACCTGCTTTCCGAGAAGGGCTTCAAACCCAAAATGTGAATCCCGCCTCCCCT

CTCACCAGAACTGTGGACTCGTCCCGGGGAGGGGCGGTGGGTGGGGCGGGGCTGGCGGGAAATTT
                                          SP1         SP1        SP1

CGG<u>TTTTGGCGCG</u>CTCCCTGCGGCGACGCTCATCGTGCGCTCTCCTCTTCCCCGGTGGTCTCCT
   E2F                                                                                  ↘ DUT-N

CGCTCGCCTTCTGGCTCTGCCATGCCCTGCTCTGAAGAGACACCCGCCATTTCACCCAGTAAGCG

GGCCCGGCCTGCGGAGGTGGGCGGCATGCAGCTCCGCTTTGCCCGGCTCTCCGAGCACGCCACGG

CCCCCACCCGGGGCTCCGCGCGCGCCGCGGGCTACGACCTGTACAGGTGAGCGGGGACCTGCCGG

CGAGGAGGCTGGGAAGGGCCGGCCGTCCGCTGCCACAGCTAGAAACAGTCACCGGAGAGATCACA

GGAACACAGTAGCTATGGGTAGGATTTCTGCCTTTTTCGTGTTTAAAATTTTAGCTTTCATCTTT

GGCATAAACCAAATAGAGATTTGGGCAAAGACTGCAGAATAAGTAAAATAGCTATACC   [SEQ ID NO:5]

FIG. 4

```
DUT-M                                              ASTVGAAGWKGELPKAGGS

DUT-N        MPCSEETPAISPSKRARPAEVGGMQLRFARLSEHATAPTRGSARAAGYDL
DUT-M        PAPGPETPAISPSKRARPAEVGGMQLRFARLSEHATAPTRGSARAAGYDL
Yeast              MTATSDKVLNIQLR----SASATVPTKGSATAAGYDL
E.coli             MKKID-VKILDPRVGKEFPLPTYATSGS---AGLDL
SRV1                SLWG-GQLCSSQQKQPISKLTRATPGS---AGLDL
MMTV                GVK-GSGLNPEAPFFPIHDLPRGTPGS---AGLDL
Visna                      SEIFLAKEGRGILQKRAED---AGYDL
EIAV                       EEIMLAYQGTQIKEKRDED---AGFDL
Orf                MEFCHTETLQVVRLSQNATIPARGSPGA---AGLDL
Vaccinia             MNINSPVRFVKETNRAKSPTRQSPYA---AGYDL
HSV1                 ELTPVQTEHGDGVREAIAFLPKREED---AGFDI
VZV                  HRDSAEYHIDVPLTYKHIINPKRQED---AGYDI DUT-N        YSAYDYTI--PPMEKAVVKTDIQIALPSGCY-GRVAPRSGLAAKHFIDVG
DUT-M        YSAYDYTI--PPMEKAVVKTDIQIALPSGCY-GRVAPRSGLAAKHFIDVG
Yeast        YASQDITI--PAMGQGMVSTDISFTVPVGTY-GRIAPRSGLAVKNGIQTG
E.coli       RACLNDAVELAPGDTTLVPTGLAIHIADPSLAAMMLPRSGLGHKHGIVLG
SRV1         SST-SHTVLTPEMGPQALSTGIYPGLPPNTFG-LILGRSSITIK-GLQVY
MMTV         SSQ-KDLILSLEDGVSLVPTLVKGTLPEGTTG-LIIGRSSNYKK-GLEVL
Visna        IC--PQEISIPAGQVKRIAIDLKINLKKDQWA-MIGTKSSFANK-GVFVQ
EIAV         CV--PYDIMIPVSDTKIIPTDVKIQVPPNSFG-WVTGKSSMAKQ-GLLIN
Orf          CS--AYDCVIPSHCSRVVFTDLLIKPPSGCYG-RIAPRSG-AVKHFIDVG
Vacc         YS--AYDYTIFPGERQLIKTDISMSMPKGCYG-RIAPRSGLSLK-GIDIG
HSV1         VVR-RPVTVPANG-TTVVQPSLRMLHADAGPACYVLGRSSLNARGLLVV-
VZV          CVP-YNLYLKRNEFIKIVLPIIRDWDLQHPSIAYIFGRSSKSRSGIIVC- DUT-N        --AGVIDEDYRGNVGVVLFNFGKEKFEVKKGDRIAQLICERIFYPE-IEE
DUT-M        --AGVIDEDYRGNVGVVLFNFGKEKFEVKKGDRIAQLICERIFYPE-IEE
Yeast        --AGVVDRDYTGEVKVVVFNHSQRDFAIKKGDRVAQLILEKIVDDAQIVV
E.coli       NLVGLIDSDYQGQLMISVWNRGQDSFTIQPGERIAQMIFVPVVQAE-FNL
SRV1         P--GVIDNDYTGEIKIMAKAVNN-IVTVPQGNRIAQLILLPLI-----ET
MMTV         P--GVIDSDFQGEIKVMVKAAKN-AVIIHKGERIAQLLLLPYL-----KL
Visna        G--GIIDSGYQGTIQVVIYNSNNKEVVIPQGRKFAQLILMPLIH-EELEP
EIAV         G--GIIDEGYTGEIQVICTNIGKSNIKLIEGQKFAQLIILQHHS-NSRQP
Orf          A--GVIDEDYRGNVGVVLFNFGNSDFEVKKGDRIAQLICERISC-PAVQE
Vacc         G--GVIDEDYRGNIGVILINNGKCTFNVNTGDRIAQLIYQRIYY-PELEE
HSV1         P--TRWLPGHVCAF--VVYNLTGVPVTLEAGAKVAQLL[]PLLV-FTNEF
VZV          P--TAWPAGEHCKF--YVYNLTGDDIRIKTGDRLAQVL[]VQWY-FTKTL DUT-N        VQALDDTERGSGGFGS-TGKN           [SEQ ID NO: 2]
DUT-M        VQALDDTERGSGGFGS-TGKN           [SEQ ID NO: 4]
Yeast        VDSLEESARGRGGFGS-TGK            [SEQ ID NO: 6]
E.coli       VEDFDATDRGEGGFGH-SGRQ           [SEQ ID NO: 7]
SRV1         DNKVQQPYRGQGSFGS-SDIYW          [SEQ ID NO: 8]
MMTV         PNPVIKEERGSEGFGSPSHVHW          [SEQ ID NO: 9]
Visna        WGETRKTERGEQGFGS-TGMYW          [SEQ ID NO:10]
EIAV         WDENKISQRGDKGFGS-TGVFW          [SEQ ID NO:11]
Orf          VNCLDNTDRGDSGFGS-TGSGA          [SEQ ID NO:12]
Vacc         VQSLDSTNRGDQGFGS-TGLR           [SEQ ID NO:13]
HSV1         DAEAPPSERGTGGFGS-TGI            [SEQ ID NO:14]
VZV          DLIATPSERGTRGFGS-TDKET          [SEQ ID NO:15]
```

FIG. 6

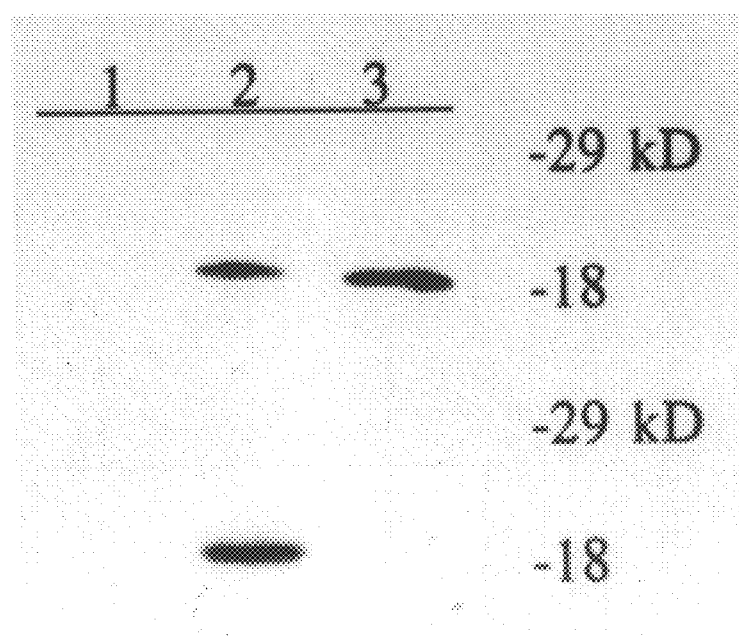

DUTPASE, ITS ISOFORMS, AND DIAGNOSTIC AND OTHER USES

This application is a continuation in part of pending provisional application Ser. No. 60/014,748, filed Mar. 29, 1996, in accordance with 35 U.S.C. §111(b), which provisional application is incorporated herein by reference.

FIELD OF THE INVENTION

The invention relates to biotechnology, and to DNA and proteins. More specifically, the invention relates to nucleic acids and proteins which are produced by cells during periods of cell proliferation. In particular, the invention relates to dUTPase and uses of duTPase as a marker for cellular proliferation and as a diagnostic and prognostic tool. The invention relates to the problem of the accurate determination of the proliferation status of a cell or a tissue, for scientific and medical applications, and contributes to the solution of this problem.

BACKGROUND OF THE INVENTION

Deoxyuridine triphosphate nucleotidohydrolase (dUTPase) is an ubiquitous enzyme which hydrolyzes deoxyuridine triphosphate (dUTP) to deoxyuridine monophosphate (dUMP) and pyrophosphate. This reaction is thought to occur primarily to limit pools of intracellular dUTP in order to prevent significant dUMP incorporation into DNA during replication and repair. A second role of dUTPase is to provide substrate (dUMP) for the de novo synthesis of thymidylate.

In both prokaryotic and eukaryotic cell systems, dUTPase has been clearly shown to be an essential enzyme, without which the cell will die. Lack of dUTPase leads to elevated cellular dUTP pools, resulting in an increased misincorporation of dUMP into DNA.

Uracil is not a native component of DNA, and efficient repair systems have evolved to remove and repair the misincorporated base. However, due to the persistent high levels of dUTP in dUTPase⁻ mutants, the repair of the misincorporated base by uracil-DNA glycosylase becomes a self-defeating repair process, resulting in the removal and subsequent reincorporation of dUMP. Ultimately, this process leads to DNA fragmentation and cell death. In addition to prokaryotes and eukaryotes, a number of viruses are known to encode a dUTPase function.

In the mammalian system, it has been shown that antifolate analogs and other inhibitors of de novo thymidylate biosynthesis cause an increase in the ratio of dUTP to dTTP resulting in misincorporation of dUMP, which further results in DNA fragmentation and cell death. It has been demonstrated that, in certain human tumor cell lines, increased levels of dUTPase are responsible for an increase in resistance to the cancer chemotherapeutic agent fluorodeoxyuridine (FUdR), a thymidylate synthetase inhibitor. These studies provide substantial evidence that dUTPase, the chief regulator of dUTP pools, mediates a critical step in FUdR toxicity.

Two groups of researchers, McIntosh et al., PNAS, 89:8020–8024 (1992) and Strahler et al., PNAS, 90:4991–4995 (1993), have reportedly isolated the human dUTPase enzyme and characterized the enzyme by its cDNA and amino acid sequences. McIntosh reported a cDNA of 526 base pairs containing an ORF which encoded a protein of 141 amino acids and a 3' flanking sequence following the ORF. Strahler reported the identical cDNA and amino acid sequence as did McIntosh, with the exception of two additional bases at the 5' end of the cDNA and a longer 3' flanking sequence. The human dUTPase reported by both groups was found to have a high degree of homology with dUTPase from other organisms including that from yeasts, bacteria and viruses. Strahler further reported that human dUTPase exists in both phosphorylated and a non-phosphorylated forms.

dUTPase in cells and phosphorylation of dUTPase occur in a cell-cycle dependent manner. That is, the level of dUTPase in the cell and the phosphorylation of dUTPase increase over resting levels during cell proliferation.

Ki-67 (mib-1) is another human protein which has been reported to increase during cell proliferation and to provide a means for assessing the growth fraction of human cells. A monoclonal antibody directed against Ki-67 has been reported to be useful to assess the growth fraction (i.e. the number of cells in cell cycle) of normal, reactive and neoplastic tissues. Brown, D. C. and Gatter, K. C., "Monoclonal Antibody Ki-67: Its Use in Histopathology", Histopathology, 17:489–503 (1990), incorporated herein by reference. Antibody Ki-67 recognizes an antigen which is associated with the cell nucleus. Various authors have reported on the cell kinetics, some reporting the increase in antigen expression with cell progression through the cell cycle in both normal and malignant cell lines, others report the uniform expression of Ki-67 antigen throughout the cell cycle. The topographical distribution of the antigen also appears to be cell cycle dependent.

It appears that the level of expression of Ki-67 is nutritionally dependent. This apparent nutritional influence on Ki-67 antigen expression is observable in the measurement of growth fraction of tumors. This nutritional phenomenon may be responsible for the variable results obtained in the growth fraction of tumors using Ki-67.

The exact function of Ki-67 antigen is not known. However, it is known that Ki-67 antigen is not essential for cell proliferation. The proliferative activity of a tumor or tissue is determined by the growth fraction (i.e. the number of cells in cell cycle) and the time taken to complete the cell cycle. There is strong correlation between the proliferation rate of tumors and clinical outcome, hence the desirability of using Ki-67 as a proliferation marker and a prognostic indicator.

However, several practical problems which limit the effectiveness of Ki-67 in that respect have been reported. Two of these shortcomings are important. First, Ki-67 antigen expression appears to be influenced by a cell's nutritional supply. Thus, tissue taken from the central area of a large tumor, which area may be necrotic, may give an erroneous low value for the growth fraction. Secondly, most tumors consist of a heterogeneous cell population, within which there are different proliferation rates. Thus, two different samples from the same tumor may give different values.

Noteworthy is that both of these practical considerations apply equally to other means of assessing growth fraction, such as tritiated thymidine and bromodeoxyuridine.

There are other shortcomings in using Ki-67 as a prognostic indicator. The growth fraction of a cell is assessable by Ki-67, but the time it takes for the cell to complete the cell cycle is not assessable by Ki-67. As a consequence, a tumor in which nearly all cells are in cycle, but where they spend a long time completing it, would show extensive positivity for Ki-67, yet the proliferation rate would not be that large. Alternatively, a tumor in which only a minority of cells are in cycle, but where the cycle time is very short, would have a higher proliferation rate, yet have few cells showing Ki-67 positivity. Thus, a limitation of Ki-67 expression is that it provides only information about whether a cell is in cycle or not, it does not tell about cell cycle length. Further, the level of Ki-67 will fluctuate during the cell cycle, and may even disappear from cells that are cycling.

Extensive studies using Ki-67 as a prognostic indicator have been reported for lymphoproliferative diseases, central nervous system tumors, collective tissue tumors, breast disease and others. Noteworthy is that it is not possible to use antibody Ki-67 to discriminate between benign and malignant breast tumors. Research-related uses of Ki-67 antibodies have raised the possibility of using the antibody to assess potential and therapeutic benefits of an antiproliferation drug such as medroxyprogesterone acetate, interferon-gamma on human endometrial carcinoma cell line. However, this work is still limited by the above noted shortcomings of Ki-67.

Several other antibodies have also been suggested to be useful as proliferation markers. These include anti-PCNA/ cyclin, anti-PAA, C5F10, and anti-DNA polymerase α. These antibodies have not gained as widespread acceptance as has Ki-67. For example, although PCNA appears to be most abundant in proliferating cells, it is also present, often at high levels, in non-proliferating cells. Therefore PCNA often yields a false positive result for proliferation.

It is evident from this review of the prior art about Ki-67 and other proliferation markers that difficult problems exist in this field of art which have yet to be resolved and that there is a serious need for a proliferation marker that will give reliable and accurate information about the status of a cell.

SUMMARY OF THE INVENTION

The following terms are defined for purposes of this specification:

"dUTPase" means any of the following, which are considered to be synonymous, "deoxyuridine triphosphate nucleotidohydrolase", "deoxyuridine triphosphate pyrophosphatase", "dUTP nucleotidohydrolase", "dUTP pyrophosphatase", and other equivalent nomenclature for the dUTPase enzyme.

"DUT-N" means the nuclear form of dUTPase.

"DUT-M" means the mitochondrial or cytoplasmic form of dUTPase.

The invention fulfills an important need and contributes to the solution of several problems confronting researchers in this field of art.

The invention provides nucleic acid and amino acid sequences of dUTPase, for both the nuclear and mitochondrial isoforms. The invention further provides the isolated gene for human dUTPase and a unique genetic system by which the two isoforms are encoded by the same gene, by means of alternative expression of 5' exons.

The invention contributes to the solution of the problem of the accurate determination of the proliferation status of cells or tissues of an organism which determination is useful in many settings, such as in assessing medical conditions and responses to therapy. The invention overcomes many of the shortcomings of the prior art by providing a reproducible and sensitive diagnostic method, based on the level of dUTPase in a cell, which allows the determination of proliferation status in any cell or tissue, from any species, in both neoplastic and normal tissues.

The invention further contributes to the solution of the problem of the determination of effective cancer chemotherapy. The DNA sequence and enzymes of the invention are useful as indicators of likely susceptibility of a cell for certain antineoplastic agents, particularly those agents which are nucleotide analogs or affect the incorporation of nucleotides into nucleic acids.

The invention further contributes to the solution of the problem of the development of effective antimicrobial and antineoplastic agents. The enzymes and DNA of the invention may be useful as effective targets for these agents. The screening of dUTPase inhibiting compounds for potential use as human therapeutic agents, such as antimicrobial and anti-cancer compounds, is thus another contribution.

The invention includes several embodiments.

One embodiment of the invention is the isolated dUTPase DNA. The dUTPase DNA of the invention has been found unexpectedly to exist in two isoforms, a nuclear form ("DUT-N") and a mitochondrial form ("DUT-M"), which differ in the length of their respective 5' ends. The discovery of the two isoforms of dUTPase has interesting potential consequences, such as those described further below. The advantages of the two isoforms is unavailable from the dUTPase as reported in the prior art which lacks the portion of the dUTPase DNA and enzyme wherein the two isoforms differ.

Another embodiment is the isolated gene which encodes both the nuclear and mitochondrial forms of dUTPase. The first exon of the ORF of the gene, from the 5' end, encodes a portion of the DUT-M protein and is spliced to the first exon which is common to DUT-M and DUT-N. The first exon of DUT-N, in contrast, is contiguous with the first common exon.

Another embodiment of the invention is the isolated dUTPase enzyme, in both the DUT-N and the DUT-M isoforms. A phosphorylation site has been discovered within 11 and 31 amino acids from the amino terminal end of DUT-N and DUT-M, respectively. The phosphorylation site may be phosphorylated or not phosphorylated. Although the phosphorylation site exists in both the DUT-N and DUT-M isoforms, only DUT-N is phosphorylated in vivo.

A further embodiment of the invention is a method for determining the proliferation status of a cell using dUTPase as a marker. dUTPase is present at low or undetectable levels in non-proliferating cells. In proliferating cells, high levels of dUTPase are present within the cell. In human cells, it has been discovered that the high levels of dUTPase produced during periods of proliferation are predominantly DUT-N within the nucleus. In contrast, DUT-M is produced at low levels independently of the cell cycle and is found within the cytoplasm.

Thus, it is the DUT-N isoform which is a proliferation marker. In contrast, DUT-M is detectable at low levels in both proliferating and non-proliferating cells. However, it has been unexpectedly discovered that certain non-proliferating neoplasms have increased levels of cytoplasmic DUT-M and are Ki-67 negative. With non-proliferating neoplasms where determination with Ki-67 and with nuclear dUTPase is negative, cytoplasmic dUTPase offers a useful prognostic value. The dUTPase determination method of the invention may be performed, if desired, in conjunction with a Ki-67 determination.

Another embodiment of the invention is a method for determining the likely response of a cancer cell to an antineoplastic agent, such as a fluoropyrimidine drug or a drug that affects thymidylate synthesis. In accordance with this method, the level of dUTPase of a cancer cell is inversely correlated with the likely degree of sensitivity of the cell to the antineoplastic agent. Conversely, the level of dUTPase in the cell is positively correlated with probable resistance of the cell to anticancer therapy. If desired, the differential determination of the absolute or relative level of one or both of the nuclear and mitochondrial forms of dUTPase may be determined, which provides further information concerning likely response of a cancer to antineoplastic agents.

Another embodiment of the invention is a kit containing the necessary reagents needed for performing the methods of the invention.

Other embodiments of the invention will become apparent from the description of the invention that follows.

The proliferation marker method of the invention overcomes several disadvantages of prior art proliferation markers.

First, unlike Ki-67, dUTPase is essential to cell viability. Without dUTPase, a cell would die. Thus, the potential for false negatives, due to loss by a proliferating cell of the ability to synthesize a proliferation marker protein, does not exist with dUTPase.

Second, because dUTPase is a stable enzyme, in contrast to Ki-67 which is rapidly degraded following cell death, it is conceivable that dUTPase may be detected for a longer period of time following cell death, at a time when Ki-67 will not be detectable any longer. This property suggests that dUTPase may be useful as a proliferation marker in cells within the necrotic centers of large tumors, which cells are Ki-67 negative.

Third, it is known that Ki-67 production is turned off in nutritionally deprived cells, even those that are proliferating. Because this does not occur with dUTPase, dUTPase will even provide information concerning proliferation in nutritionally deprived cells. Further, as opposed to the fluctuating levels of Ki-67 during the cell cycle, dUTPase levels remain constant and detectable.

Fourth, certain tumors, which test negative for proliferation with Ki-67, test positive when tested for dUTPase in accordance with the method of the invention.

Fifth, dUTPase is an ideal proliferation marker because the two isoforms of dUTPase are readily distinguishable from each other, for example by location in the cell, allowing for accurate assessment of proliferation. This is in contrast to other proteins which are produced in relation to the cell cycle, such as uracil-DNA glycosylase, which exists in at least six isoforms, some of which are produced irrespectively of the cell cycle.

BRIEF DESCRIPTION OF THE DRAWINGS

FIG. 1 shows the nucleotide and amino acid sequences, Seq. ID Nos. 1 and 2 respectively, of the nuclear form of dUTPase, DUT-N.

FIG. 2 shows the nucleotide and amino acid sequences, Seq. ID Nos. 3 and 4 respectively, of the cytoplasmic form of dUTPase, DUT-M.

FIG. 4 shows a sequence analysis of the 5' region of the human dUTPase gene (Seq. ID No. 5). Numbering of the nucleotide positions was arbitrarily chosen. The beginning of the DUT-M and DUT-N sequences are indicated by arrows. Consensus sequences for NFkB, SP1 and E2F binding have been underlined.

FIG. 6 shows a comparison of the amino acid sequence of human DUT-N and DUT-M with that of known dUTPases, as shown in Seq. ID Nos. 6 to 15.

FIG. 19 shows site directed mutagenesis analysis of the phosphorylation site of DUT-N at Ser-11.

DETAILED DESCRIPTION OF THE INVENTION

Figure 3:
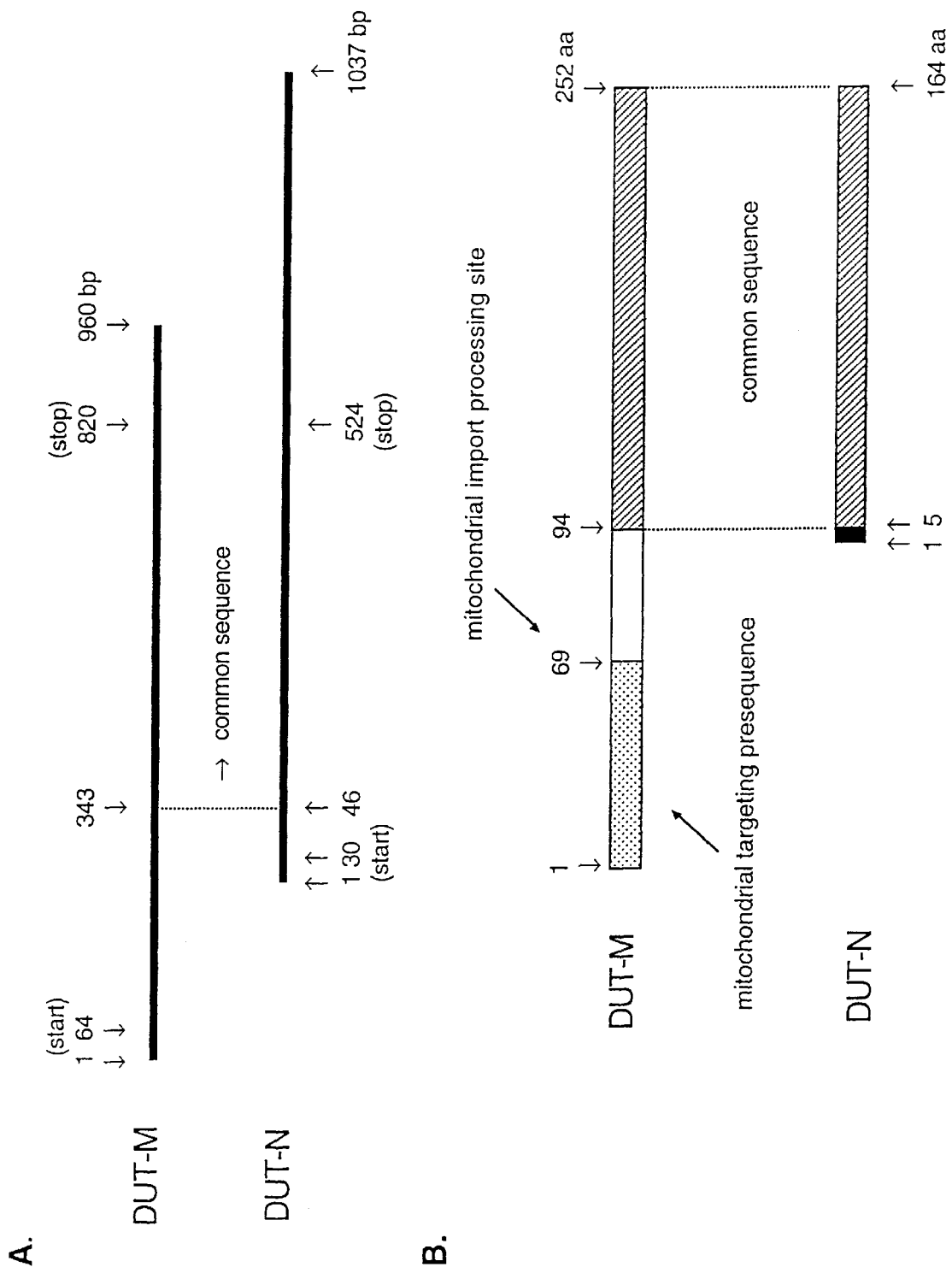
FIG. 3 shows a comparison of the cDNA and amino acid sequences of DUT-N and DUT-M. A. Schematic illustration comparing the cDNA sequences of DUT-N and DUT-M isoforms. Translation initiation and termination codons are indicated. B. Comparison of DUT-N and DUT-M protein sequences.
Figure 5:
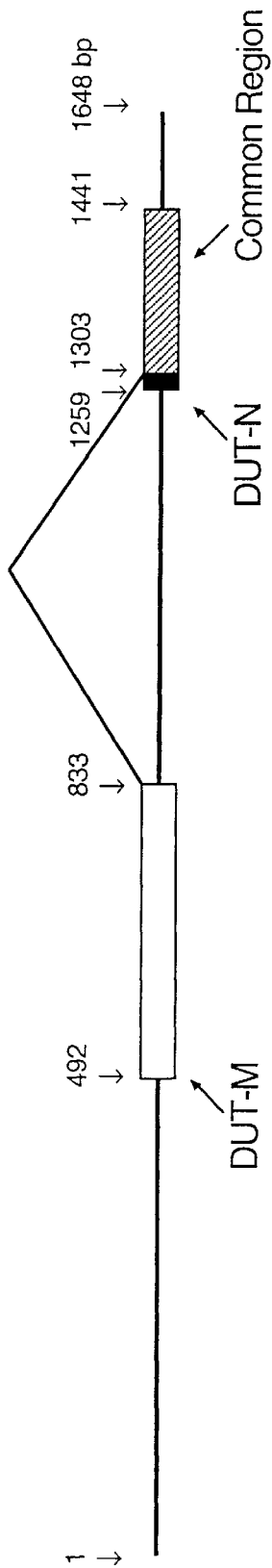
FIG. 5 shows a schematic illustration of the 5' region of the human dUTPase gene. Exons are boxed and open reading frames of DUT-M, DUT-N and common sequences are distinguished by different shading. Intron/exon boundaries are indicated and numbered with respect to the complete nucleotide sequence in FIG. 10. The N-terminal DUT-M splice junction is indicated by joining lines.

The invention provides the isolated and purified complete human dUTPase gene; also, the sequenced complete DNA for human dUTPase; and the isolated and purified complete human dUTPase enzyme. In addition, it has been discovered unexpectedly that there exist two isoforms of human dUTPase, a nuclear form designated DUT-N and a cytoplasmic form designated DUT-M, which is targeted to the mitochondria. The DNA sequences for DUT-N and DUT-M are shown in FIGS. 1 and 2, and Seq. ID Nos. 1 and 2, respectively. The amino acid sequences for DUT-N and DUT-M are shown in FIGS. 1 and 2, and in Seq. ID Nos. 2 and 4, respectively.

The DNA sequence of the 5' end of the gene encoding both DUT-N and DUT-M is shown in FIG. 4 and in Seq. ID No. 5. The isoforms arise by the use of alternative 5' exons which then join a common sequence. The 5' exon of DUT-M is spliced to the common sequence while the 5' exon of DUT-N is contiguous with the common sequence. Exon 1 of DUT-M correlates with position 528 through 869 of the genomic isolate. There is a DUT-M-specific intron between position 870 and 1338 with a splicing event occurring between exon 1 of DUT-M and the first exon shared between the isoforms. Consensus donor and acceptor splice sites are located at positions 869 and 1339 respectively.

In contrast, the DUT-N isoform is encoded beginning at position 1295 and is continuous with the first common exon. After the first common exon there is an intron corresponding to position 1477 of the genomic isolate. A consensus donor splice site is located at position 1477. An exon containing a portion of the common carboxy terminus shared by both DUT-N and DUT-N lies approximately 15 kb further downstream.

It has been further discovered that the DNA for human dUTPase of the invention surprisingly differs from that reported in the prior art in several respects.

The ORF of the human dUTPase DUT-N gene of the invention encodes a protein having 164 amino acids. The isolated DUT-N dUTPase of the invention contains an additional 23 amino terminal amino acids which were not reported in the prior art. The ORF of the human dUTPase DUT-M gene encodes a protein having 184 amino acids, an additional 43 amino acids which were not reported in the prior art.

Additionally, the DNA of the invention does not enode a cytosine with nuclleotides 84–86, as shown in FIG. 1 and Seq. ID No. 1, in contrast to the prior art which reports an encoded cytosine at this position. Further, the dUTPase DNA of the invention, as shown in Seq. ID No. 1, contains a sequence of 528 bases located 3' to the ORF, which were not reported in the prior art.

It was also unexpectedly discovered that the serine amino acid at position 11 of DUT-N is the sole phosphorylation site of the protein. This phosphorylation site corresponds to the consensus target sequence for the cyclin dependent protein kinase p34$^{cdc2}$. This discovery was all the more surprising in light of the disclosures by Strahler and McIntosh of a sequence for human dUTPase which lacks the serine-11 phosphorylation site.

Unexpectedly, the two isoforms of the human dUTPase enzyme are found to be virtually identical, differing, however, in their production in relation to the cell cycle, their localization within the cell, the length of their 5' ends, and the in vivo presence or absence of phosphorylation of the serine residue closest to the amino terminal.

The DUT-N isoform is located within the nucleus of the cell and is produced at low or undetectable levels during non-proliferative periods of the cell cycle. In contrast, the DUT-M isoform is found within the cytoplasm and is targeted to the mitochondria independently of the cell cycle. There are certain tumors, however, which produce increased amounts of DUT-M during periods of non-proliferation. These non-proliferating tumors in which an increased amount of DUT-M is detectable, are not detected by Ki-67 and test negative for DUT-N.

DUT-N and DUT-M each contain the same amino acid sequence beginning with residue number 6 (glutamate) of DUT-N, as shown in FIG. 1. The portions of the two isoforms 5' to this residue differ. DUT-N contains an amino acid sequence of MPCSE (Seq. ID No. 2) 5' to the glutamate residue. DUT-M contains an amino acid sequence of ASTV-GAAGWKGELPKAGGSPAPGP (Seq. ID No. 4) 5' to the glutamate residue. Thus, the differences between the nuclear and the mitochondrial forms of dUTPase are determined to be in the amino terminal domains, which is in the non-conserved region of the protein.

In vitro transcription and translation of the DUT-M cDNA results in the production of a precursor protein with an apparent molecular weight of 31 kD as judged by SDS-PAGE. The DUT-M precursor is enzymatically active and immunoreacts with a dUTPase specific monoclonal antibody. Mitochondrial import and processing studies demonstrate that the DUT-M precursor is processed into a 23 kD protein and imported into mitochondria in vitro. Isoelectric focusing experiments demonstrate that the DUT-N has a pI of 6.0 while the processed form of DUT-M has a more basic pI of 8.1, measurements that are in agreement with predicted values.

In vivo, the DUT-N isoform is post-translationally phosphorylated at the serine residue at position 11, within the consensus sequence for cyclin dependent kinase phosphorylation, and is specifically phosphorylated by p34$^{cdc2}$. Although this serine residue is present in the DUT-M isoform, DUT-M remains non-phosphorylated within the cell.

The amino acid sequence of the human dUTPase of the invention is highly homologous to dUTPase of other organisms, including rat, tomato, yeast and various bacteria and viruses. See FIG. 6 and Seq. ID Nos. 6–15. As shown, there are at least five well conserved domains in the various species illustrated. Because of the high degree of homology between humans and other species, including lower single celled eukaryotic and prokaryotic species and viruses, it is conceived that the dUTPase of all higher animals and plants likewise have a similar or higher degree of homology to the human protein.

The nucleotide sequences and the dUTPase isoforms of the invention have various utilities described further herein.

The DNA sequences of the invention are useful, for example, to create specifically altered vectors for site-directed mutagenesis or to transiently or stably transfect cells or tissues with functional dUTPase.

The dUTPase enzyme of the invention is useful as a marker for cellular proliferation. The determination of proliferation is highly useful in tumor diagnosis, prognosis, and response to therapy, in determining responses to tissue grafts in which proliferation of cells suggests rejection, or to evaluate proliferation in affected areas post-surgically. Another important use for the dUTPase, and for the two isoforms of dUTPase, is as an indicator of the likely efficacy of an antineoplastic drug, such as fluoropyrimidine drugs or drugs that affect thymidylate synthesis, in killing neoplastic cells. Because these drugs cause misincorporation of uracil or its analogs into DNA, high levels of dUTPase indicates resistance to the drugs, whereas lower levels of dUTPase indicates sensitivity. Thus, high or low levels of either or both of the isoforms of dUTPase can be correlated with resistance or sensitivity to an anticancer compound. In addition, the dUTPase can be used in combination with certain antineoplastic drugs, such as pyrimidine analogs, to test the efficacy of the drugs in killing neoplastic tissues, in a patient or in vitro, and the adverse effect of the drugs on normal, non-neoplastic tissues.

The dUTPases of the invention are also useful as a target for the development of antineoplastic or antimicrobial agents, such as antiviral, antibacterial, or antifungal drugs, which agents act by inhibiting dUTPase, which in turn kills the cell or organism. The dUTPase may also be used to develop antibodies specific for animal species, such as mice or rats, to measure proliferation and dUTPase levels for screening drugs believed to inhibit nucleotide metabolism, such as the fluoropyrimidine drugs.

A determination of dUTPase is useful to determine the apoptotic state of a neoplastic cell, either before or following antineoplastic therapy. A positive correlation has been determined between Bcl-2 expression, a protein marker which inhibits apoptosis, and DUT-M expression in cancer cells. It is believed that Bcl-2 may stimulate production of dUTPase, which in turn may protect a cell from anticancer drugs, such as fluoropyrimidine drugs.

An interesting use is based on the discovery of the dUTPase isoforms and the different properties between Ki-67 and the cytoplasmic isoform of dUTPase of the invention. In certain non-proliferating tumors, cytoplasmic dUTPase will offer useful diagnostic and/or prognostic information when both Ki-67 and nuclear dUTPase are negative.

In accordance with the diagnostic method of the invention the proliferative status of a cell or cells is determined by removing the cell from a body, labelling the dUTPase contained within the cell, ascertaining the amount of dUTPase in the cell, and comparing the amount of dUTPase in the cell to that in a control cell of which the proliferation status is known. It is also conceivable that the diagnostic method of the invention may be performed without first removing a cell from the body or that the amount of dUTPase in a cell may be determined without labelling the dUTPase.

Resting cells typically have a low level of diffusely distributed dUTPase throughout the cytoplasm, and little or no detectable dUTPase in the nucleus. In contrast, proliferating cells have a high level of dUTPase in the nucleus, in addition to the diffuse cytoplasmic dUTPase. Consequently, if the level of dUTPase in the test cell is high, the cell is determined to be in a proliferation stage of the cell cycle. In contrast, if the level of dUTPase in the cell is low or undetectable, the cell is in a non-proliferative stage of the cell cycle.

The amount of dUTPase in the test cell is generally compared to that of a control cell in which the cell cycle stage and the qualitative or quantitative amount of dUTPase is known. The level of dUTPase in the control cell may be determined before, after, or simultaneously with that of the test cell. Typically, a control slide containing cells known to be positive (and/or negative) for dUTPase, either DUT-N or DUT-M, is run in parallel to a slide containing the test cells. Alternatively, the control cell may be an historic control, such as a photograph of a resting or proliferating cell in a textbook if the relative amounts of dUTPase are to be determined qualitatively, or as a numerical figure if the relative amounts of dUTPase are to be determined quantitatively or the results of dUTPase determination may be compared with results obtained with Ki-67.

The cell tested may be any type of cell from any species that makes dUTPase. Suitable species include humans, other animals such as mammals, reptiles, amphibians, and birds, fish, invertebrates, protozoa, plants such as fungi, dicotyledonous and monocotyledonous plants, and bacteria. In addition, because certain viruses promote the production of dUTPase, the method of the invention may be used to diagnose infection of a cell by such a virus.

Because dUTPases from different species share a high degree of homology, the DNA and the enzymes of the invention can be used to design a probe to isolate the dUTPase DNA or enzyme from a non-human cell. Following this, the diagnostic method of the invention may be performed for determining dUTPase in a non-human cell in the manner described herein for dUTPase in human cells.

The cell tested may be a cancerous or a non-cancerous cell and may originate from any organ. The control cell may originate from the same organism as the test cell or may originate from a different organism, generally of the same species. The test cell may or may not be from the same tissue type as the control cell.

The cell or cells to be tested may be removed from the body by any means which permits the amount of dUTPase in the cells to be determined. Preferably, the cells are living at time of removal, although this is not obligatory. Examples of suitable methods for removal from the body include surgical excision, biopsy, needle aspiration, and separation of cells from bodily fluids, such as cerebrospinal fluid, saliva, ascites, urine, mucus, or blood. In the case of plants, cells may be removed for example by cutting or by aspiration. Cells in culture, such as animal, plant, or bacterial cells, are treated as cells which have been removed from a body. These cells may by tested in situ or may be removed from the culture medium. Conceivably, a non-invasive procedure may be developed in the future.

The determination of the amount of dUTPase present in the cell may be performed by any means which accomplishes this determination. Determination of the level of dUTPase may be by qualitative "eye-balling" or may be by a more quantitative method, such as by cell counting. Any method of determination of the level of dUTPase in the test cells which allows for a comparison to that of control cells is suitable for the method of the invention.

In a preferred procedure, the dUTPase may be immunohistologically labelled by means of an antibody, such as a monoclonal antibody, specific for the dUTPase of that species. Means of making monoclonal antibodies specific for a protein are known. See for example, Coligan et al., "Current Protocols in Immunology", John Wiley & Sons, Inc., which is herein expressly incorporated by reference.

An alternative procedure of labelling dUTPase in the cell is to radioactively label the dUTPase of the test cell by incorporation of radioactive phosphorus at the DUT-N dUTPase phosphorylation site, which is then detected by known techniques, such as Western blotting. A second alternative means of labelling dUTPase in the cell is by means of radioactively labelled methionine, which is a metabolic label.

The cells, either before or after labelling depending on the method of labelling, may be formalin fixed and paraffin embedded, and mounted on a slide. The dUTPase of the test cell is labelled by contacting the mounted cells to a labelled monoclonal or polyclonal antibody specific for dUTPase. A secondary antibody, such as a fluorescent or biotin labelled antibody, may be used, which antibodies may be detected by means of an enzyme-linked assay that yields a visible light chromogen. The labelled cells mounted on the slide may be used as a permanent record of the proliferation status of the cells. These slides may be used to provide a permanent record of the proliferation status of the cells upon the slide and may be used as a baseline for later comparison of cells from the same or a different tissue or individual.

Following labelling, the cells may be examined by an appropriate means to determine the presence or absence of detectable levels of dUTPase in the cell. For example, by visual examination antibody-tagged cells may be determined by microscopic evaluation of the cells in histological specimens. The radioactively phosphorylated cells or cells metabolically labelled by radioactive methionine may be determined by immunoprecipitation.

Figure 7A:
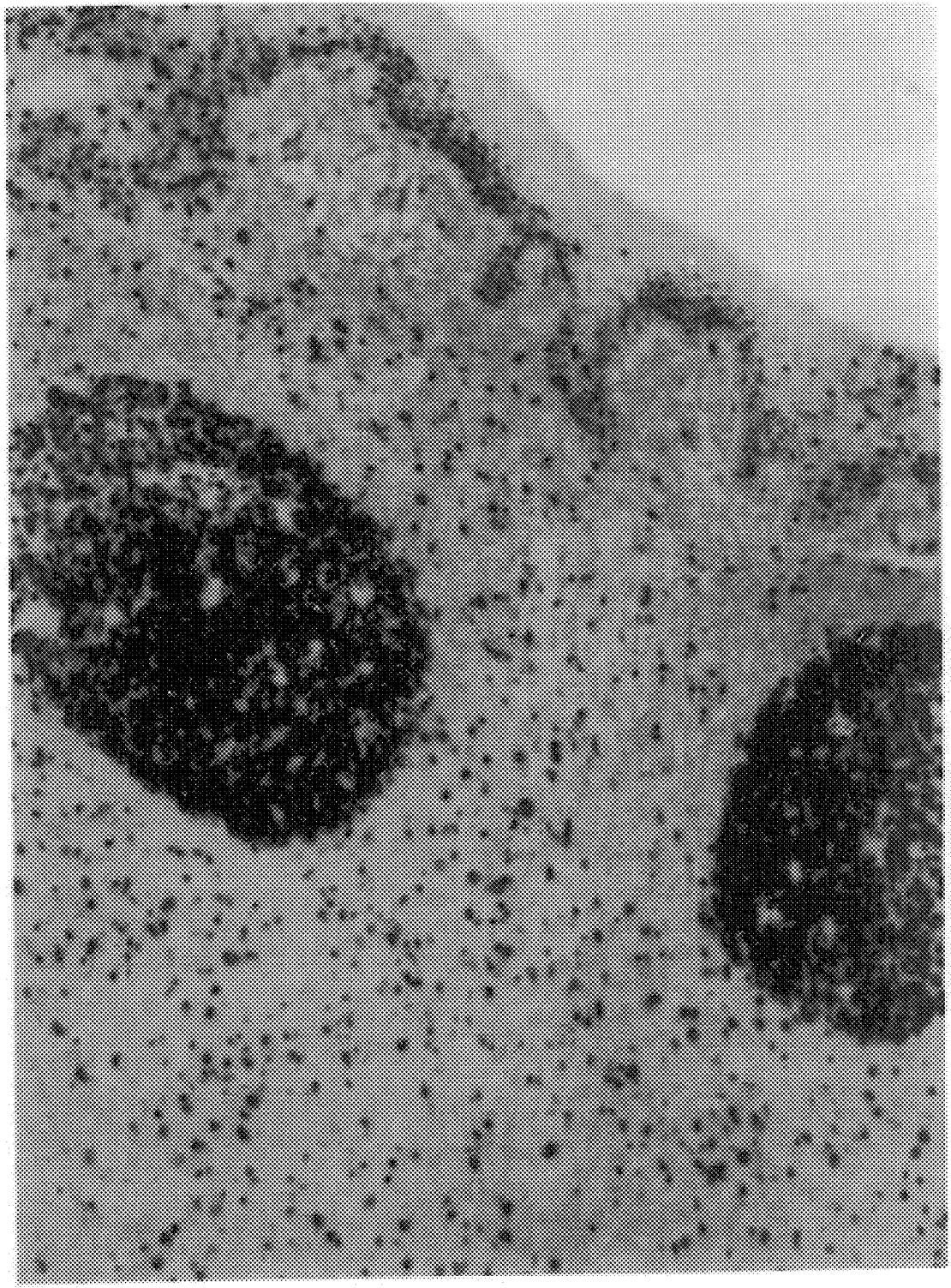
FIG. 7 shows immunohistochemical determination of dUTPase in normal human tonsil stained with an anti-dUTPase mAB.
Figure 7B:
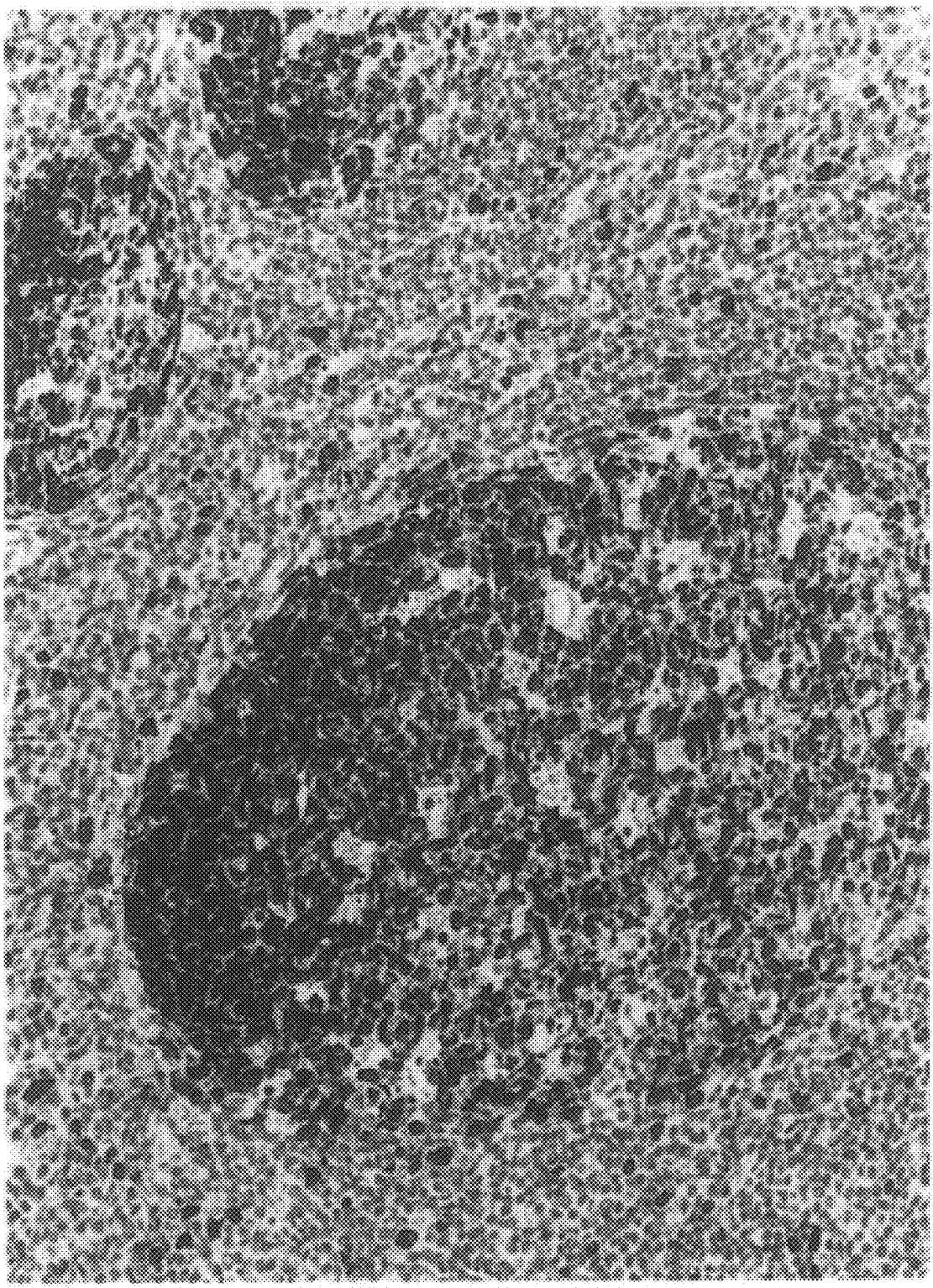
Figure 7C:
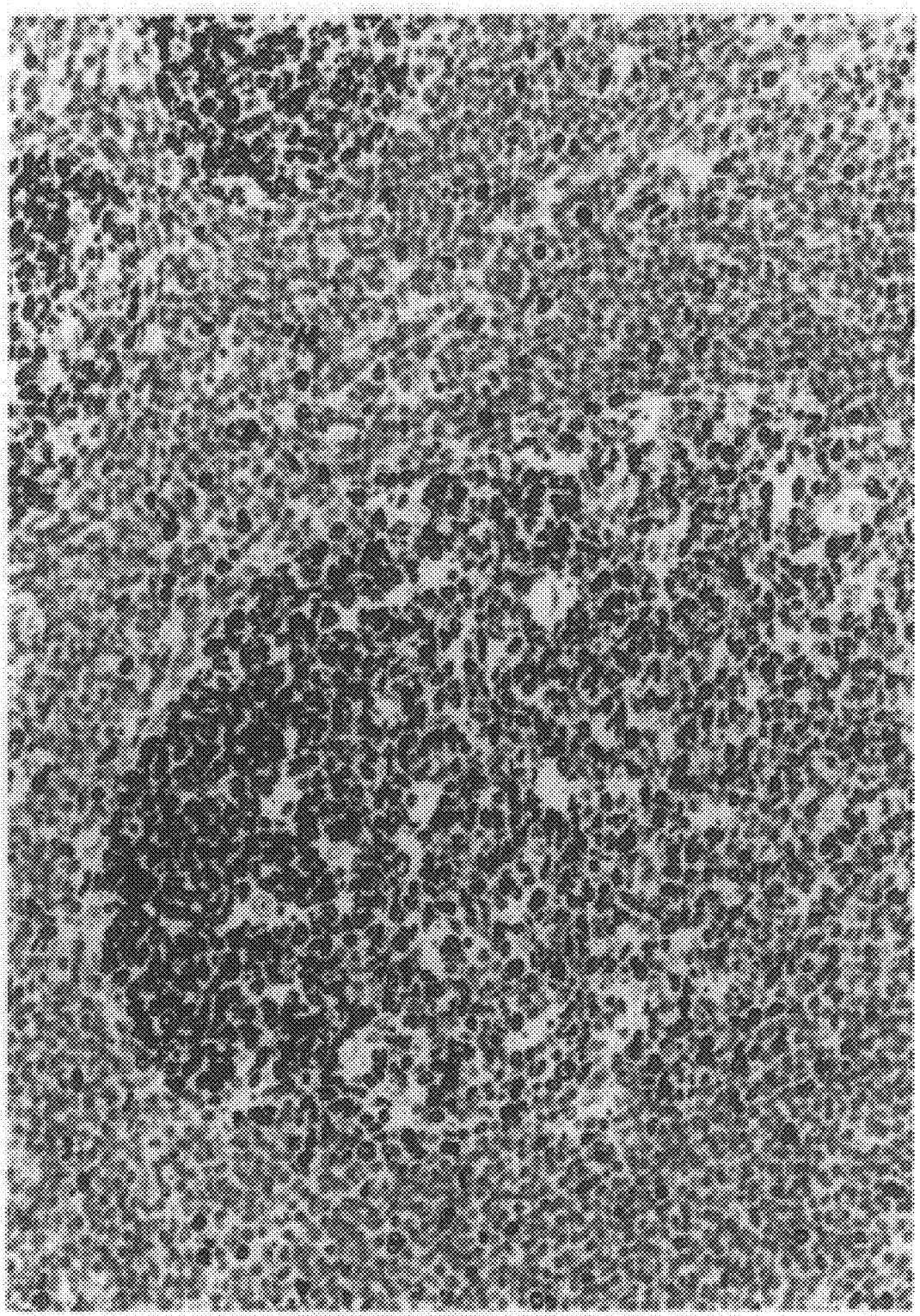
Figure 8:
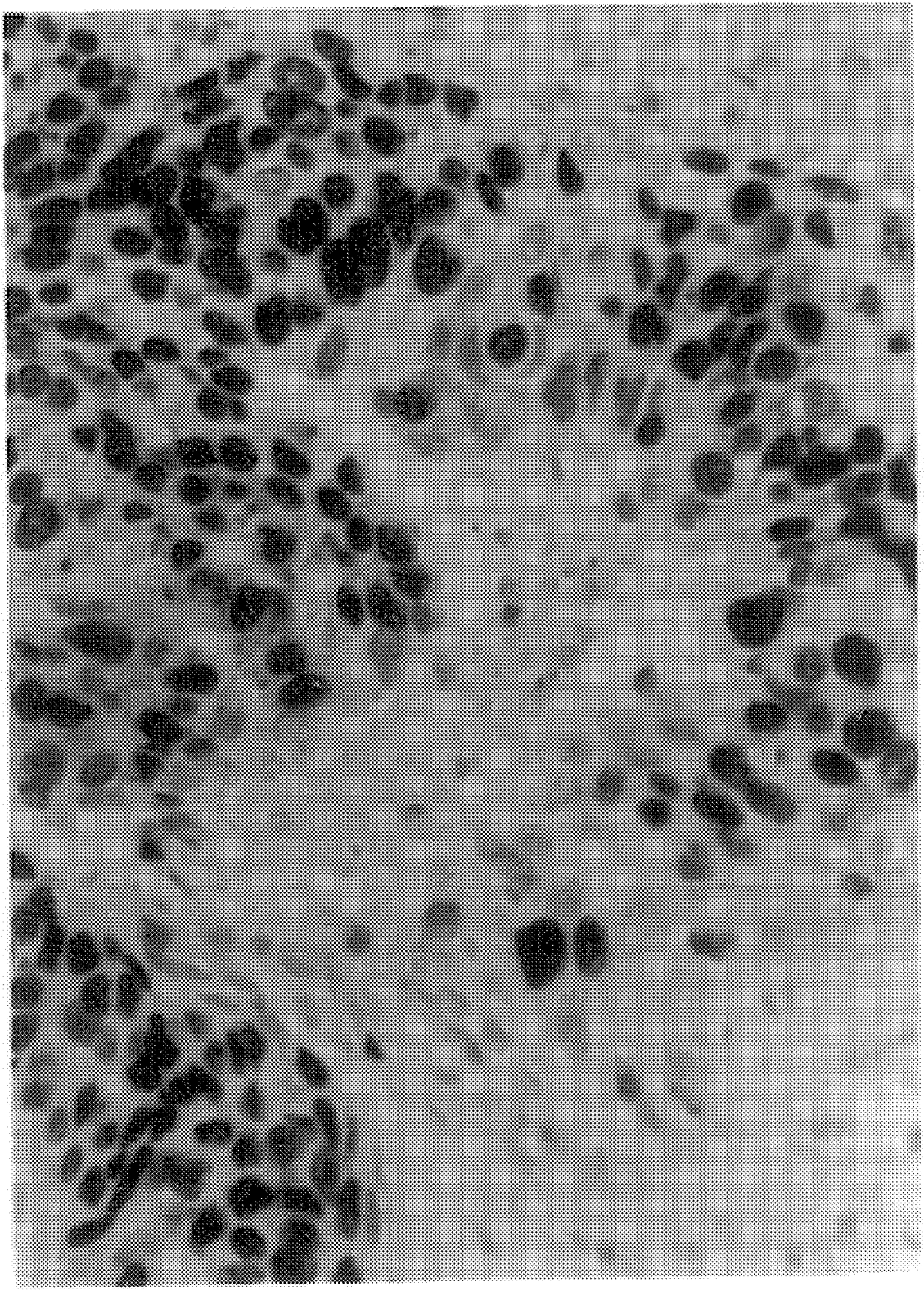
FIG. 8 shows immunohistochemical determination of dUTPase in a human metastatic adenocarcinoma stained with an anti-dUTPase mAB.
Figure 9:
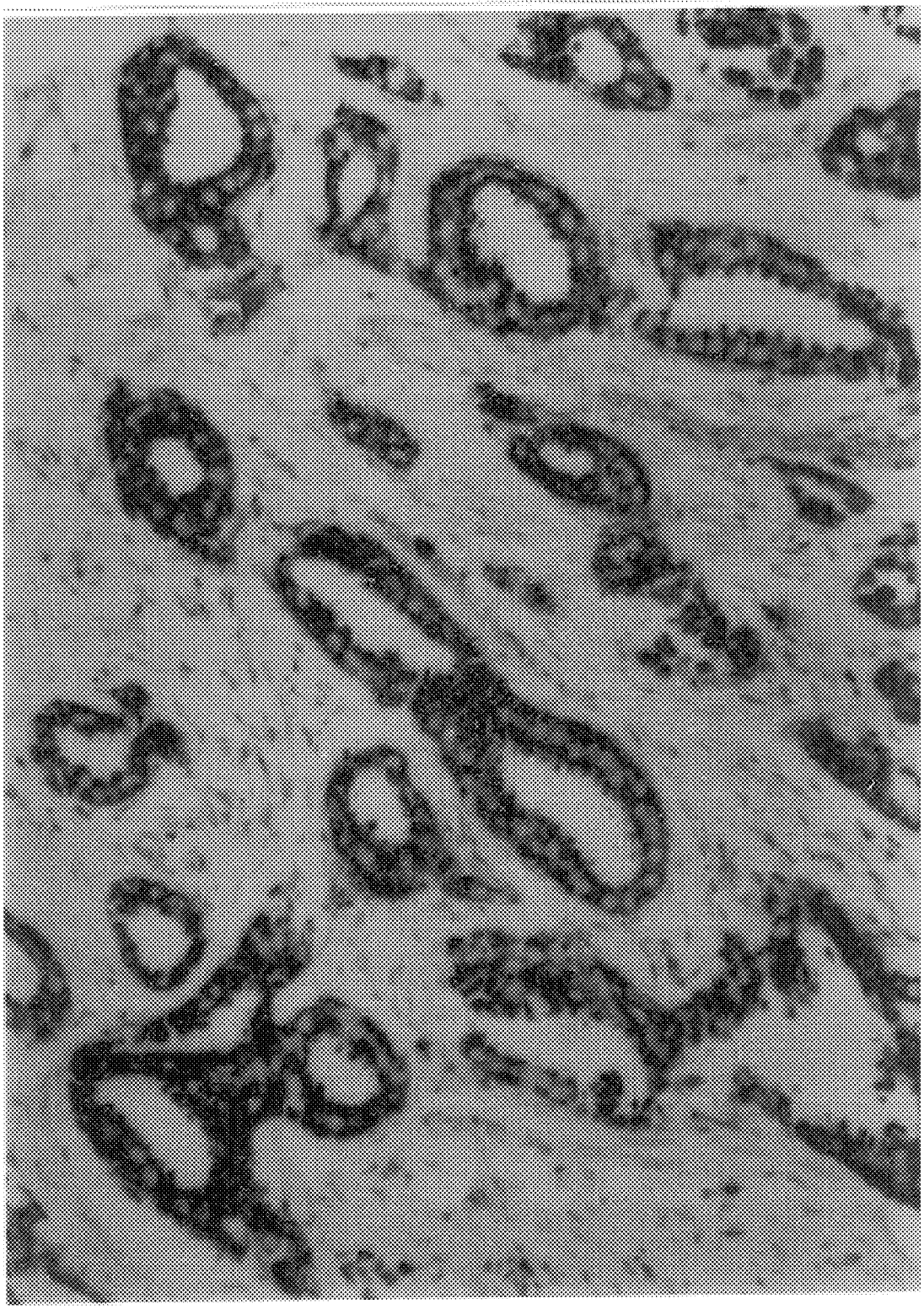
FIG. 9 shows immunohistochemical determination of dUTPase in a human breast ductal carcinoma.

FIGS. 7 to 9 show immunohistochemical determination of dUTPase in normal human tonsil, a human metastatic adenocarcinoma, and a well-differentiated, infiltrative human breast ductal carcinoma, each of which was stained with an anti-dUTPase mAB. FIG. 7 illustrates intense nuclear staining by the dUTPase mAb in proliferative germinal centers and basal layer epithelium of normal human tonsil. FIG. 8 illustrates an example of the specific nuclear localization of dUTPase staining in a metastatic adenocarcinoma. FIG. 9 illustrates intense cytoplasmic staining in the neoplastic ductal cells. The tissue shown in FIG. 9 was negative for Ki-67 staining.

If desired, the specific presence or absence of DUT-N, the form of dUTPase which is localized in the nucleus, may be determined. Typically, non-proliferating cells have little or no detectable levels of dUTPase in the nucleus. Proliferating cells, in contrast, have large amounts of concentrated nuclear dUTPase.

Because the extra-nuclear isoform of dUTPase, DUT-M, is found in the cytoplasm in both non-proliferating cells and proliferating cells, the determination of DUT-M often does not yield information relevant to a determination of the proliferation status of a cell. However, as shown in FIG. 9, certain cells which are Ki-67 negative have increased amounts of DUT-M in the cytoplasm. It is believed that the increase in DUT-M in these cells is indicative of anti-apoptosis events or the general biochemical state of the cell.

Figure 10A:
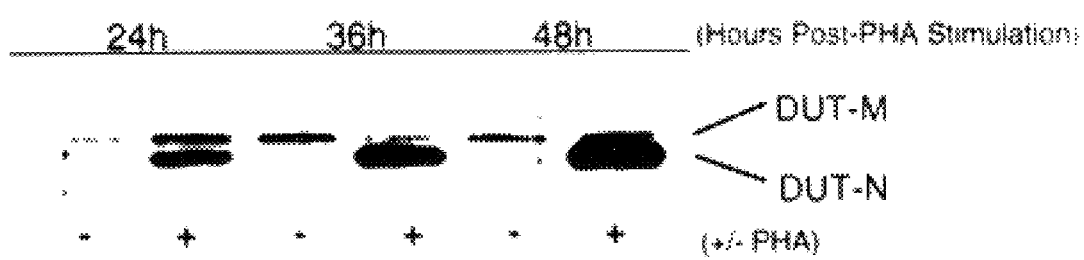
FIG. 10 shows the use of Western blot analysis to determine the level of dUTPase in resting and proliferating cells, and the comparison of the level of dUTPase to that of radioactive thymidine uptake.
Figure 10B:
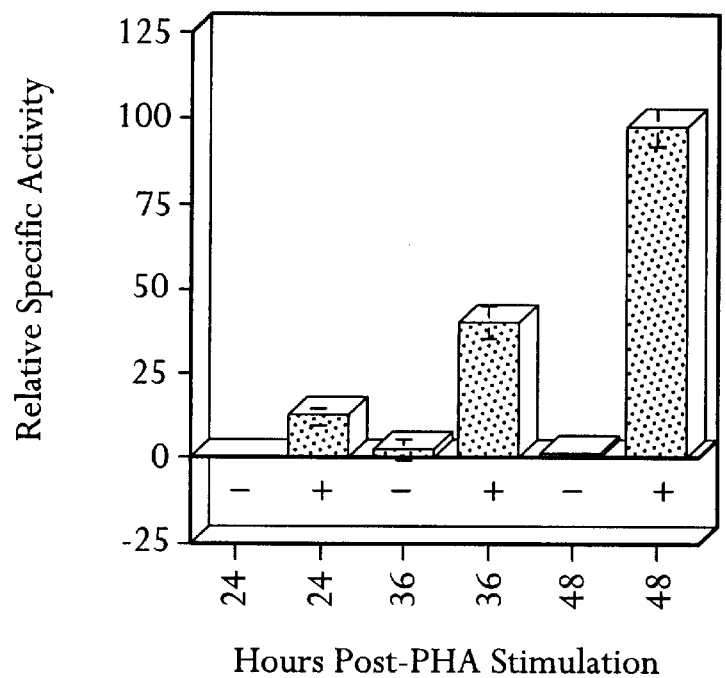
Figure 10C:
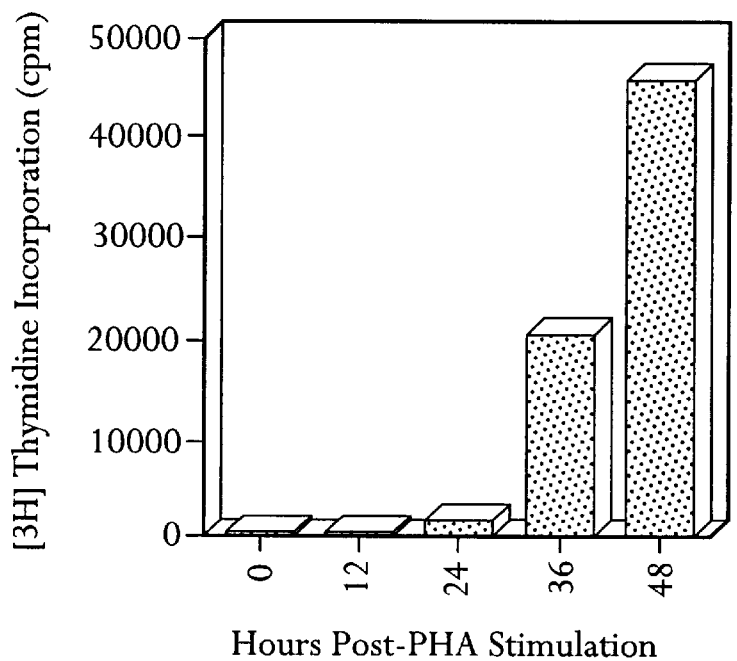

FIG. 10 shows the use of Western blot analysis to determine the level of dUTPase in cells. Peripheral blood lymphocytes (PBL) that were stimulated to proliferate with phytohemagglutinin (PHA) were compared with unstimulated cells. FIGS. 10A and B show that, at 24, 36, and 48 hours post-stimulation, the stimulated cells had greatly increased levels of dUTPase, which was predominately the DUT-N isoform. FIG. 10C shows that the increase in DUT-N correlates well with the uptake of radioactive thymidine, indicating DNA synthesis, establishing that the DUT-N levels are indicative of cellular proliferation.

The method of the invention is useful to determine changes in the proliferation status of a cell or a tissue due to various stimuli, including chemical, mechanical and electrical stimulation. Additionally, most neoplastic cells and tissues have a higher proliferation rate than their non-neoplastic counterparts. Less well differentiated tumors tend to have a higher rate of proliferation than more differentiated tumors. Thus, the method of the invention can be used as an aid in the diagnosis, prognosis, or monitoring of cancer, and to assist in determining the state of differentiation of a cell. If desired, the method of the invention may be performed sequentially to monitor changes in proliferation status of the cells of a tissue over time. The type of tumor is immaterial to the method of the invention because all proliferating cells require dUTPase. Thus, the method of the invention, when applied to neoplastic tumors, is applicable to both benign and malignant tumors, and to both sarcomas and carcinomas.

The method of the invention is also useful to determine the effect of various anti-cancer chemotherapeutic agents on the proliferative rate of cells, both target neoplastic cells and normal non-neoplastic cells. Thus, the method of the invention can be used as a means of monitoring response to therapy of cancer.

In addition, the method of the invention can be used to determine the effect of an anti-cancer chemotherapeutic agent on dUTPase and the dUTP/dUMP cellular equilibrium. In this way, the effectiveness or the likely effectiveness of a drug on the treatment of a cancer can be evaluated. The cell to be tested may be treated with an anticancer agent either prior to, after, or simultaneously with the determination of dUTPase by the method of the invention. Suitable agents which can be evaluated in this manner include those drugs which affect the incorporation of uracil and/or thymidine into DNA, such as pyrimidine analogs or chemicals which alter the function of thymidylate synthase. Examples suitable agents whose action can be evaluated in this way are 5-fluorouracil, floxuridine, fluoro-2'-deoxyuridine, idoxuridine, cytosine arabinoside, azauridine, and azaribine or others with similar biological action that may be synthesized in the future.

The invention provides a kit which contains the necessary reagents for performing the method of the invention to determine the proliferative status of a cell. The components of the kit may vary depending on the labelling and detection methods employed. For example, if the labelling method is by fluorescent antibody, the kit contains an antibody specific for dUTPase, which antibody carries a fluorescent marker. If desired, the kit may additionally contain reagents and chemicals for fixing and mounting a tissue sample on a slide. Alternatively, if the labelling method is by radiolabelling the phosphorylation site of DUT-N, the kit may contain radioactively labelled orthophosphate.

A preferred kit of the invention is a dUTPase protein detection kit which kit includes an antibody specific for dUTPase which recognizes dUTPase in immunohistochemical tissue or cell preparations, a labelled secondary antibody, such as a biotin labelled secondary antibody, an enzyme link, such as a peroxidase, and a chromogen substrate for the enzyme link, such as DAB (brown permanent chromogen).

Another kit is a dUTPase biochemical assay kit to determine the amount of dUTPase protein in a total protein preparation from a cell or tissue, such as a tumor. This determination may be useful in evaluating the resistance or sensitivity of the tumor to certain antineoplastic drugs. The kit contains an antibody specific for dUTPase, which antibody is tagged with beads similarly to the dextran charcoal assays used to measure estrogen and progesterone levels in breast biopsy preparations.

Other kits of the invention include a dUTPase detection kit by Western or immunoblot, a dUTPase DNA detection kit by Southern blot, a dUTPase RNA detection kit by Northern blot, and a specific mitochondrial dUTPase antibody kit.

Another kit is a dUTPase enzyme kit for the detection of bacterial, viral, or fungal infection based on the presence or absence of the particular pathogenic species' dUTPase. This kit may contain an antibody specific to the species' dUTPase, a labelled secondary antibody, an enzyme link, and a chromogen enzyme substrate.

The following examples are illustrative of the invention and are not intended to be interpreted as limiting the scope of the invention. One skilled in the art may develop equivalent means and/or reactants without the exercise of inventive capacity and without departing from the scope of the invention.

EXAMPLE 1

Purification of dUTPase

HeLa S3 cells (CCL 2.2) were purchased from American Type Culture Collection and maintained in Dulbecco's modified Eagle's medium supplemented with 5% fetal calf serum purchased from GIBCO-BRL. Sf21 cells for baculovirus expression of dUTPase were purchased from Clontech Laboratories, Inc. and maintained in Grace's insect cell media supplemented with yeastolate, lactalbumin hydrolysate and 10% fetal bovine serum (GIBCO-BRL).

Cellular extracts were partially purified by streptomycin sulfate fractionation, ammonium sulfate fractionation, DEAE-cellulose and phenyl-sepharose chromatography as described Caradonna and Adamkiewicz, J. Biol. Chem., 259:5459–5464 (1984), incorporated herein by reference. This partially purified fraction was then subjected to immunoaffinity chromatography. dUTPase specific monoclonal antibodies were bound to cyanogen bromide activated sepharose (Sigma) according to standard protocols. dUTPase derived from the phenyl-sepharose chromatography step was dialyzed against 20 mM Tris-HCl pH 7.5, 1 mM EDTA, 10% glycerol and 150 mM NaCl and then incubated with the antibody-sepharose overnight at 4° C. with gentle agitation. The matrix was applied to a column and washed with 10 bed volumes of wash buffer containing: 20 mM Tris-HCl pH 7.5, 1 mM EDTA, 10% glycerol and 0.5M NaCl. dUTPase was eluted with 25 ml of 100 mM glycine pH 2.5. Fractions (1 ml) were collected, neutralized by the addition of 100 μl of 2M Tris-HCl pH 8.0 and assayed for dUTPase activity. Peak fractions were pooled and dialyzed against 20 mM Tris-HCl pH 7.5 and 10% glycerol. Purified protein was fractionated by 15% SDS-PAGE and silver stained.

EXAMPLE 2

Two different forms of dUTPase

Figure 11:
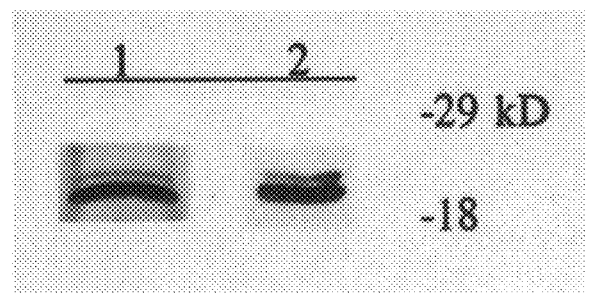
FIG. 11 shows silver staining and Western blot analysis demonstrating existence of the two isoforms of the dUTPase enzyme.

Fractionation by SDS-PAGE and silver staining of purified dUTPase from HeLa S3 cells revealed two closely migrating protein species which immunopurified using a monoclonal antibody against human dUTPase. See FIG. 11, lane 1. The lower molecular weight species (DUT-N) was found to be at least 30-fold more abundant than the higher molecular weight species (DUT-M) as determined by densitometry. Immuno-blot staining polyclonal antibodies were generated using a recombinant form of the DUT-N protein expressed in the baculovirus system. Western blot analysis of total HeLa cell extract demonstrated that both protein forms immunostain with the polyclonal antisera (FIG. 11, lane 2), indicating that the two proteins share common epitopes and represent unique isoforms of the dUTPase protein.

EXAMPLE 3

Cellular Fractionation: Isolation of Mitochondria and Nuclei from HeLa Cells.

Cellular fractionation and purification of mitochondria was performed according to the procedure of Rickwood et al., Mitochondria, a Practical Approach, 1–16, IRL Press (1987), incorporated herein by reference. HeLa cells were washed twice in cold PBS and resuspended in ice-cold homogenization buffer (0.25M sucrose, 1 mM EGTA, 10 mM Hepes-NaOH pH 7.4 containing 0.5% BSA). The cells were homogenized in a glass-teflon homogenizer using 10 strokes at 500 r.p.m. The homogenate was centrifuged at 1500×g for 10 min at 4° C. to pellet nuclei and unbroken cells. Approximately 10% of the crude post-nuclear supernatant was saved and used as the "cytosolic extract" in Western blot experiments. The remainder of the post-nuclear supernatant was centrifuged at 10,000×g for 10 min at 4° C. to pellet mitochondria. The mitochondrial pellet was resuspended in 0.8M sucrose, 1 mM EDTA, 0.1% BSA and 10 mM Tris-HCl pH 7.5 and gently layered on continuous sucrose gradients from 1–2M sucrose containing 1 mM EDTA, 0.1% BSA and 10 mM Tris-HCl, pH 7.5. The gradients were centrifuged for 2 hours at 80,000×g at 4° C. The brown band of intact mitochondria was removed with a Pasteur pipette, diluted with 2 volumes of 1 mM EDTA, 10 mM Tris-HCl pH 7.4 and the pure mitochondria pelleted by centrifugation at 20,000×g for 10 min at 4° C. The purified mitochondrial pellet was resuspended in 20 mM Tris-HCl pH 7.5, 1 mM EDTA and 150 mM NaCl and mitochondria disrupted by sonication. The mitochondrial extract was centrifuged at 10,000×g for 30 min to remove insoluble debris. The resulting mitochondrial protein extract was used for subsequent immunoblot analysis or purification of mitochondrial-associated dUTPase by the method described above.

Purified nuclei were obtained according to the hypotonic shock procedure described by Dignam et al., Nuc. Acids Res., 11:1475–1489 (1993), incorporated herein by reference. HeLa cells grown in suspension culture were pelleted by centrifugation at 800×g for 15 min. The cells were washed once in cold PBS and resuspended in five volumes of buffer A (10 mM HEPES pH 7.9, 1.5 mM $MgCl_2$ 10 mM KCl and 0.5 mM DTT). The cell suspension was allowed to sit for 10 min on ice and then the cells were collected by centrifugation (800×g for 5 min). Cells were suspended in two volumes of buffer A and disrupted by 10 strokes of a Kontes glass homogenizer (B type pestle). Nuclei were pelleted by centrifugation (800×g for 5 min). The post-nuclear supernatant was discarded and the nuclear pellet was washed twice in 5 volumes of buffer A by dounce homogenization with a Kontes homogenizer and B type pestle. At this point essentially 100% of the cells were disrupted and all the nuclei stained intensely with trypan-blue vital stain as judged by phase-contrast microscopy.

The nuclear pellet was next resuspended in 10 mM Tris-HCl (pH 7.6), 1 mM $CaCl_2$, 1 mM $MgSO_4$ and 35%

(w/v) Nycodenz (GBCO-BRL). The nuclear suspension was subjected to isopycnic density gradient centrifugation on Nycodenz by layering the nuclear suspension (6 ml) on a step gradient of 50% (3 ml) and 40% (3 ml) Nycodenz solution as described by Ford and Graham, An Introduction to Centrifugation, Bios Scientific Publishers, Oxford, pages 79–81 (1991), incorporated herein by reference. The gradient was centrifuged for one hour at 10,000×g in a SW41 rotor at 4° C. The nuclei, banding at the 40/50% Nycodenz interface were removed and washed twice in buffer A. The nuclei were finally resuspended in NP40 buffer (50 mM Tris-HCl pH 7.5, 0.25M NaCl, 0.1% NP40, 5 mM EDTA) and sonicated extensively to disrupt nuclear structure. The nuclear extract was centrifuged at 10,000×g for 30 min to remove insoluble debris. The resulting nuclear extract was utilized for subsequent immunoblot analysis or purification of the nuclear-associated dUTPase by the method described above.

Figure 12:
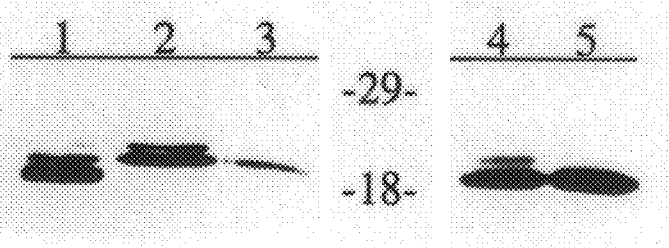
FIG. 12 shows Western blot analysis of dUTPase from total cell extracts (lanes 1 and 4), cytosolic extracts (lane 2), purified mitochondria (lane 3), and purified nuclei (lane 5).

As demonstrated in FIG. 12, lanes 1 and 4, two species of dUTPase are readily detected in total HeLa cell extract. Immunostaining of protein derived from purified mitochondria demonstrates the exclusive mitochondrial association of the higher molecular weight species of dUTPase, DUT-M (FIG. 12, lane 3). Western blot of the cytosolic extract (FIG. 12, lane 2) shows the presence of the putative mitochondrial form. There is also an additional higher molecular weight species detected in this fraction. This immunoreactive protein may represent a precursor form of the mitochondrially targeted dUTPase, suggesting that DUT-M represents the fully processed form of mitochondrial dUTPase.

Western blot analysis of purified mitochondrial protein (FIG. 12, lane 3) and cytosolic extract (FIG. 12, lane 2) demonstrates a complete lack of the more abundant, lower molecular weight form of dUTPase, DUT-N, suggesting that this form is localized exclusively within the nucleus. In order to verify the specific nuclear localization of this form, nuclei were purified and dUTPase protein detected by western blot analysis. FIG. 12, lane 5 indicates that the more abundant, lower molecular weight form of dUTPase, DUT-N, is associated with the purified nuclei.

EXAMPLE 4

Enzyme Assays of dUTPase activity dUTPase activity was measured using the procedure described by Caradonna and Adamkiewicz, J. Biol. Chem., 259:5459–5464 (1984). All reactions were performed in a 10 $\mu$l volume containing 20 mM Tris-HCl pH 7.5, 50 $\mu$M MgCl$_2$, 2 mM dithiothreitol, 50 $\mu$M dUTP, and 1 $\mu$M ($^3$H)-dUTP (400 mCi/mmol, Amersham). Reactions were performed at 37° C. for 5 min. Reactions were terminated by the addition of 2 $\mu$l of nucleotide markers (10 mM each) and EDTA (50 mM). 2 $\mu$l aliquots were applied to polyethyleneimine-cellulose (Sigma) and the plates were developed with 0.5M LiCl, 2M acetic acid at room temperature. The dUMP, dUDP and dUTP spots were visualized under UV light, excised, and radioactivity determined by liquid scintillation counting. K$_m$ values were determined as described in Caradonna and Adamkiewicz.

EXAMPLE 5

Isolation and Sequencing of the Nuclear dUTPase DNA

A human T-cell cDNA library in lambda gt10 was purchased from Clontech. The library was screened using a synthetic oligonucleotide probe based on the amino acid sequence of DUT-N and the human dUTPase DNA sequence reported in the EMBL/Genbank Data Libraries; 5' AAGAGACACCCGC- CATTTCACCCAGTAA 3', Seq. ID No. 16. The library screening protocol was based on standard procedures as described by Sambrook, et al., Molecular Cloning: A Laboratory Manual, 2d ed., Cold Springs Harbor Laboratory, Cold Spring Harbor, N.Y. (1989), incorporated herein by reference.

The cDNA library was plated at a density of 35,000 plaques/100-cm$^2$ dish. After 6 hours of growth the plates were incubated at 4° C. for 1 hour. Nitrocellulose lifts were prepared in duplicate and baked at 80° C. for 2 hours. Prehybridization was conducted in 5 X SSC, 10 X Denhardt's solution, 0.5% SDS, 0.3% tetrasodium pyrophosphate and 100 $\mu$g/ml denatured salmon sperm DNA for 2 hours at 68° C. The oligonucleotide probe was $^{32}$p end-labeled and hybridization carried out in the same solution for 12–16 hours at 68° C. Filters were washed four times in 6 X SSC, 0.1% SDS at 68° C. for 10 min each. Two 10 min washes at 71° C. in 2 X SSC, 0.1% SDS were then performed. The membranes were air dried and exposed to Kodak XAR film for 24 to 36 hours. Out of 43 positive clones identified, ten clones were chosen for subsequent rounds of plaque purification. Two cDNA isolates (1.1 kb and 0.9 kb) were subcloned into the EcoRI site of pGEM-3Z (Promega). These clones were sequenced using the Sequenase dideoxy chain termination kit (United States Biochemical Corp.) according to the manufacturer's recommendations. Bal-31 exonuclease was used to generate a series of deletion clones in order to sequence the entire cDNA. The sequence was determined from both strands.

EXAMPLE 6

Isolation and Sequencing of the Mitochondrial dUTPase cDNA

A $\lambda$gt10 cDNA library was constructed from mRNA derived from serum starved 34 Lu human lung fibroblasts (CRL 1491) obtained from American Type Culture Collection. The cells were maintained in Eagle's minimal essential medium (MEM) supplemented with 10% fetal calf serum purchased from Life Technologies Inc. Total RNA was isolated using the reagents and protocols of TRIZOL Reagent (Life Technologies Inc.). Poly (A)$^+$ RNA was purified with the PolyATtract mRNA Isolation System (Promega). cDNA construction was performed using the Superscript Choice System for cDNA Synthesis (Life Technologies Inc.). The library was screened using a 935 bp, SphI/EcoRI fragment of the DUT-N cDNA, which contains sequence common to both DUT-N and DUT-M isoforms. The library screening protocol was based on standard procedures as described by Sambrook, et al. (20). Several cDNA isolates were subcloned into the EcoRI site of pGEM-3Z (Promega). These clones were sequenced using the Sequenase dideoxy chain termination kit (U.S. Biochemical Corp.) according to the manufacturer's recommendations. A series of subclones were generated using internal restriction sites to facilitate sequencing of the cDNA isolates in their entirety. The sequences were determined from both strands.

EXAMPLE 7

Isolation of the Human dUTPase gene

An EMBL-3 human leukocyte genomic library (CLONTECH) was screened with the DUT-N cDNA. The library screening protocol was based on standard procedures as described by Sambrook, et al. (20). Several clones were isolated and the largest of which (15 kb) was further characterized by a combination of restriction digestion, Southern hybridization and sequence analysis. An oligonucleotide probe (5'-GGTGTCTCTTCAGAGCAGG-3') Seq. ID No. 17 corresponding to the extreme 5' end of the DUT-N cDNA was synthesized and used to identify a 2.7 kb EcoRI/BamHI genomic fragment. This fragment was subsequently sequenced using a series of nested sequencing primers designed from newly obtained sequence information.

EXAMPLE 8

Expression of Recombinant dUTPase from Cloned cDNA

The coding region of the DUT-N gene was subcloned into the baculovirus expression vector pBacPAK8 (Clonetech) and dUTPase overproduced in Sf21 insect cells as per the manufacturer's recommendations. The resulting recombinant protein was purified by the method described above and shown to be functional by enzyme assay (Km=2.5 μM).

EXAMPLE 9

Antibody Production and Western Blot Analysis dUTPase specific monoclonal antibodies were generated and prepared as described by Lirette and Caradonna, J. Cell. Biochem., 43:339–353 (1990), incorporated herein by reference. These antibodies are useful for immunoprecipitation and immuno-affinity chromatography. dUTPase specific polyclonal antibodies, useful for immuno-blot analysis, were raised against recombinant DUT-N protein (expressed in the baculovirus system) according to procedures outlined by Harlow and Lane, Antibodies: A Laboratory Manual, Cold Spring Harbor Laboratory, Cold Spring Harbor, N.Y. (1988), incorporated herein by reference. The antibodies were then purified by immuno-affinity chromatography.

10–15 mg of purified recombinant DUT-N protein was bound to cyanogen bromide-activated sepharose by standard protocols. The dUTPase polyclonal antisera was then incubated with the dUTPase-sepharose overnight at 4° C. with gentle agitation. The sepharose was applied to a column and washed with 10 bed volumes of 20 mM Tris-HCl pH 7.5, 1 mM EDTA and 0.5M NaCl. The dUTPase specific antibody was eluted with 100 mM glycine pH 2.5 and subsequently dialyzed against several changes of phosphate buffered saline at 4° C. The resulting immunopurified dUTPase specific polyclonal antibody was used at a dilution of 1:1000.

Protein was fractionated by 15% SDS-PAGE and transferred to nitrocellulose according to Towbin, et al., Proc. Nat. Acad. Sci., 76:4350–4354 (1979), incorporated herein by reference. The membrane was blocked in TBST (10 mM Tris-HCl pH 8.0, 150 mM NaCl and 0.05% Tween 200 containing 5% powdered skim milk). dUTPase specific polyclonal antibodies were added into the blocking solution at a dilution of 1:1000 and the blot was incubated with rocking overnight. The blot was then washed five times with 10 ml of TBST. The blot was subsequently incubated for 1 hour in secondary antibody (goat anti-rabbit IgG conjugated to horse radish peroxidase, GIBCO-BRL) diluted 1:4000 in blocking solution. The blot was washed five times in TBST and the protein bands visualized with the ECL chemiluminescent western blotting detection system (Amersham), using the detection protocol as provided by the manufacturer.

EXAMPLE 10

Differential Expression of Nuclear and Mitochondrial Isoforms of dUTPase in Serum Stimulated and Starved Human Fibroblasts- 34 Lu human lung fibroblast cells were serum starved for 72 h and subsequently serum stimulated by the addition of 10% FBS to the media. DNA replication status was monitored by [$^3$H]-thymidine incorporation at the indicated time points. Cells were harvested at time points correlating with $G_0$, $G_1$, and S phase (as monitored by [$^3$H]-thymidine incorporation) and equivalent amounts of total cellular protein were fractionated by 15% SDS-PAGE. The protein was transferred to nitrocellulose and dUTPase isoforms were detected by immunoblot analysis.

Figure 13A:
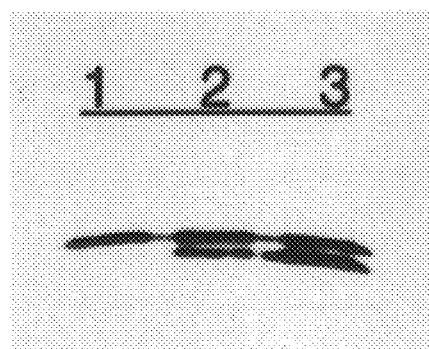
FIG. 13 shows expression of dUTPase isoforms during serum stimulation of 34 Lu human lung fibroblasts. A. 34 Lu cells were driven into $G_0$ by serum starvation for 72 h. Lane 1, 0 h ($G_0$); lane 2, 12 h ($G_1$ phase); lane 3; 30 h (S phase). Equivalent amounts of protein were loaded in each lane. B. [$^3$H]-thymidine incorporation was utilized to monitor DNA replication status during serum stimulation of 34 Lu cells. At the indicated time points post-stimulation, cells were pulsed for 20 min with [$^3$H]-thymidine and subsequent incorporation of radioactivity into DNA was determined.
Figure 13B:
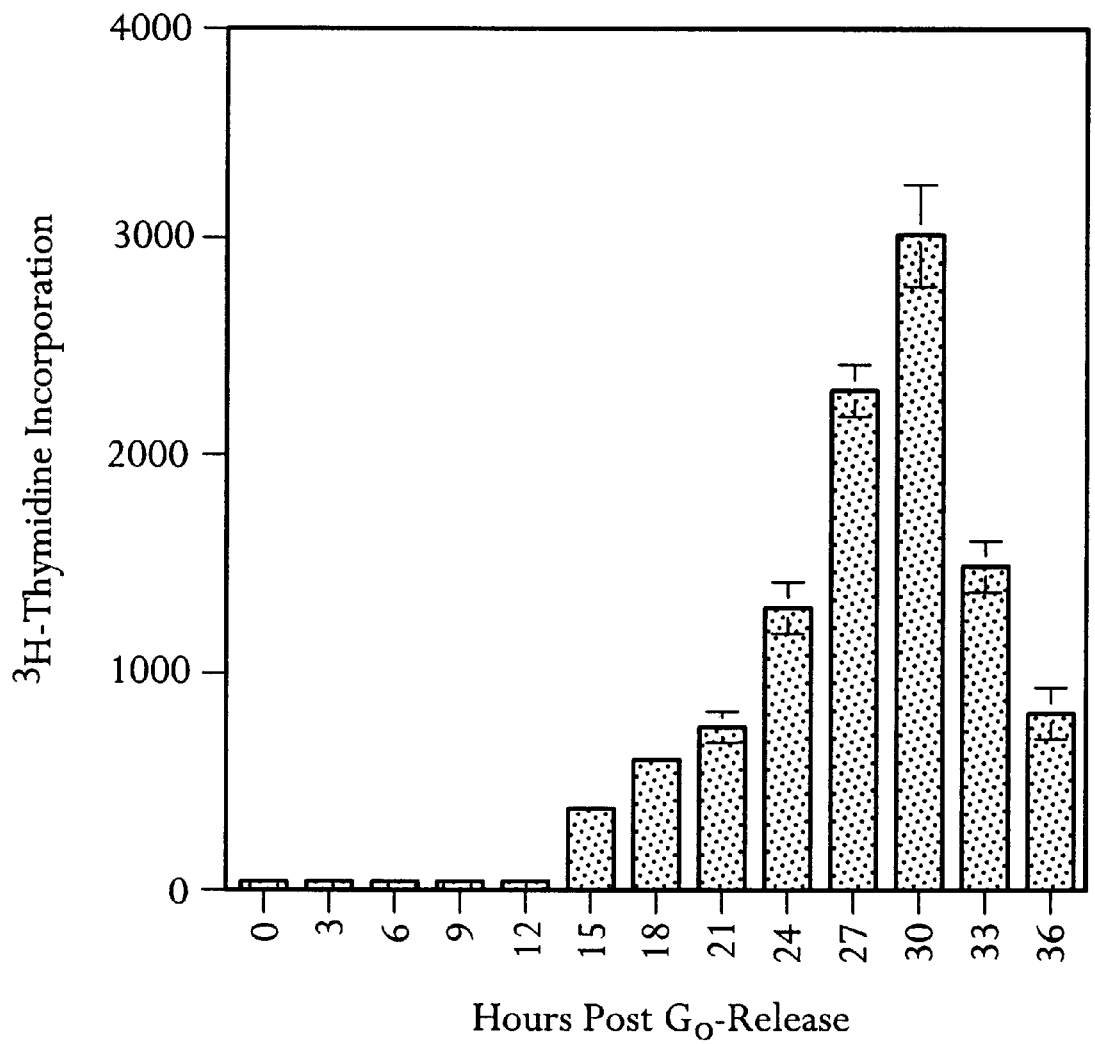

Time course experiments presented in FIGS. 13A and 13B illustrate dUTPase expression in response to serum stimulation. The Western blot presented in FIG. 13A illustrates dUTPase expression status in cells 0 h post-stimulation (lane 1), in cells 15 h post-stimulation (lane 2), and in cells 36 h post-stimulation (lane 3). The lower molecular weight DUT-N isoform is induced in response to serum stimulation, correlating with the onset of DNA replication (see FIG. 13B). In contrast, the higher molecular weight DUT-M isoform is expressed in a constitutive manner, independent of proliferation status.

Figure 14A:
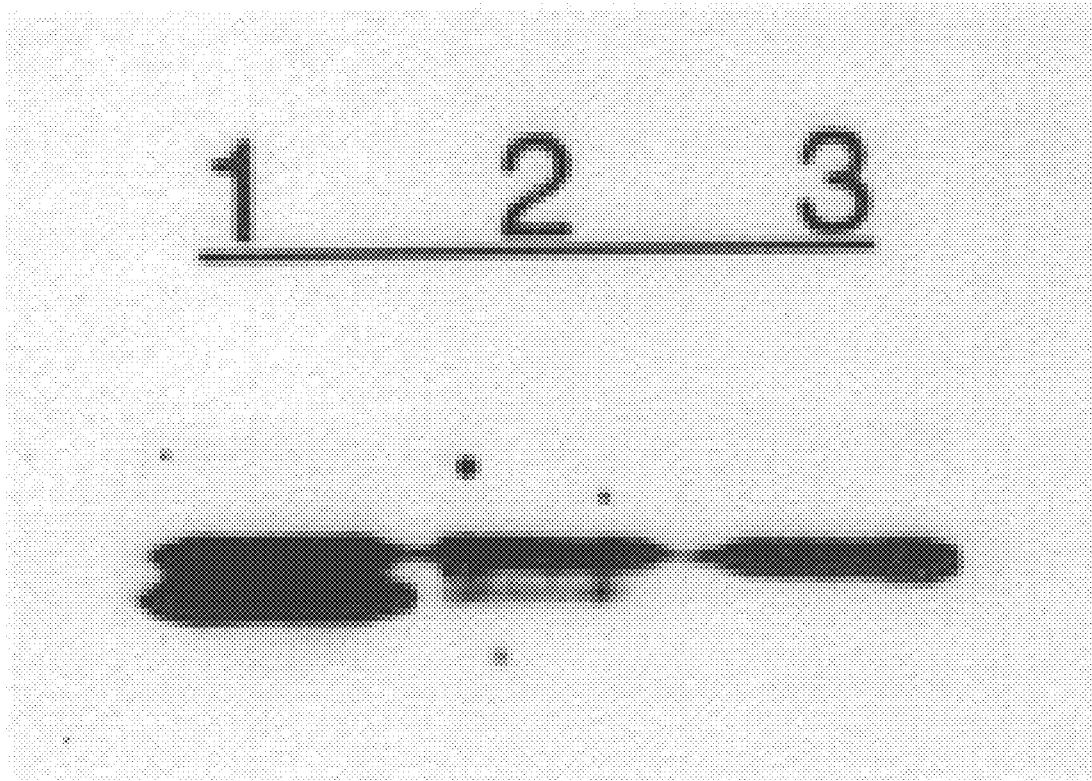
FIG. 14 shows expression of dUTPase isoforms during serum starvation of 34LU human lung fibroblasts. A. Cycling 34 Lu cells were driven into Go by serum starvation. Protein samples were collected at 0, 24 and 48 hours post-starvation. Samples were fractionated by 15 SDS-PAGE and dUTPase protein was detected by Western blot analysis utilizing dUTPase-specific polyclonal antibodies. Lane 1, 0 h; lane 2, 24 h and lane 3, 48 h. B. Thymidine incorporation was utilized to monitor DNA replication during serum starvation. At the indicated time points post-starvation, cells were pulsed for 20 min with [$^3$H]-thymidine and subsequent incorporation of radioactivity into DNA was determined.
Figure 14B:
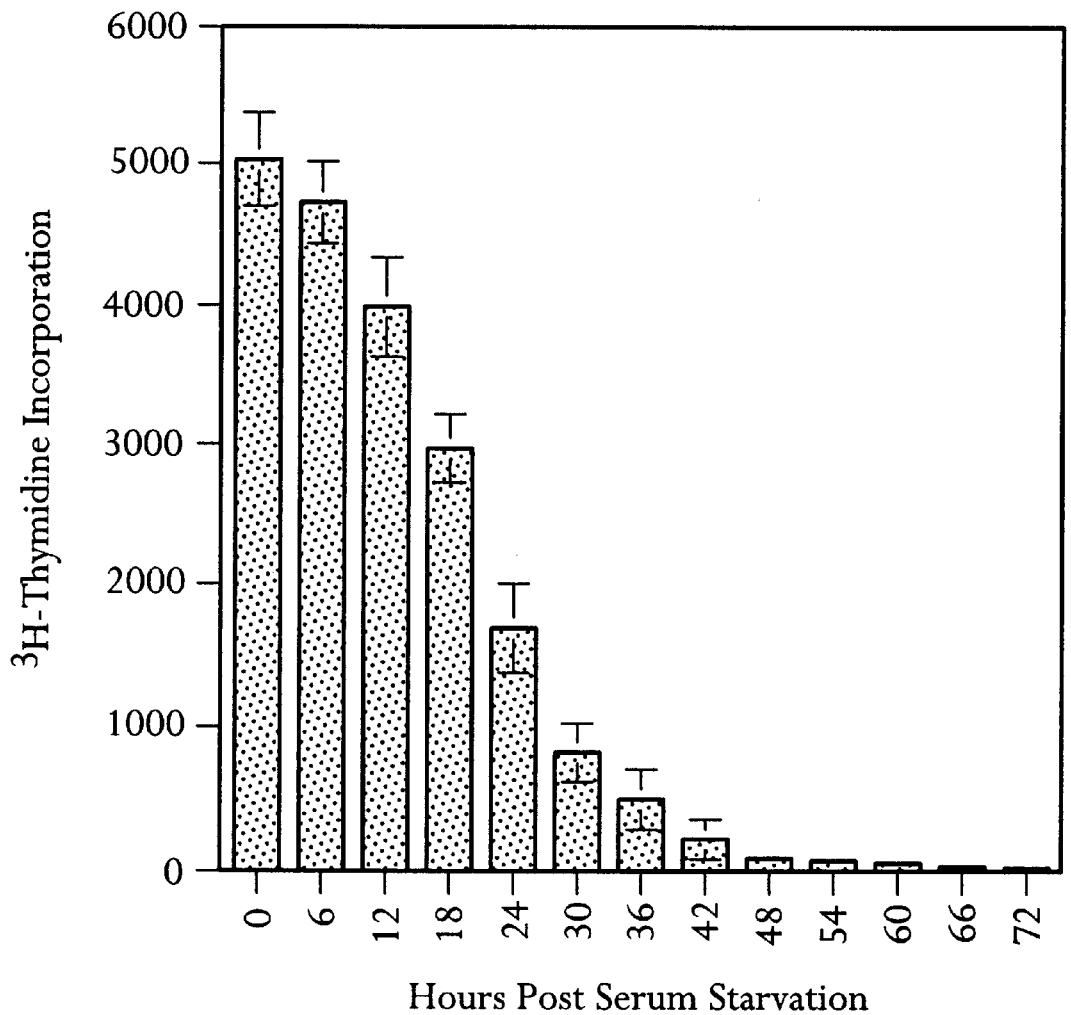

A similar time course study was performed to demonstrate that differential dUTPase isoform expression is a consequence of serum-starvation. Cycling cells were serum starved and dUTPase expression monitored by Western blot. FIG. 14, lane 1 illustrates dUTPase expression at 0 h, lane 2 at 24 hours post-starvation and lane 3 at 48 h post-starvation. These data indicate that DUT-N is preferentially degraded within 72 h post-starvation; a rate that corresponds with the cessation of nuclear DNA replication (FIG. 14B). DUT-M levels however, remain constant as the cells transition into the $G_0$ state.

Figure 15A:
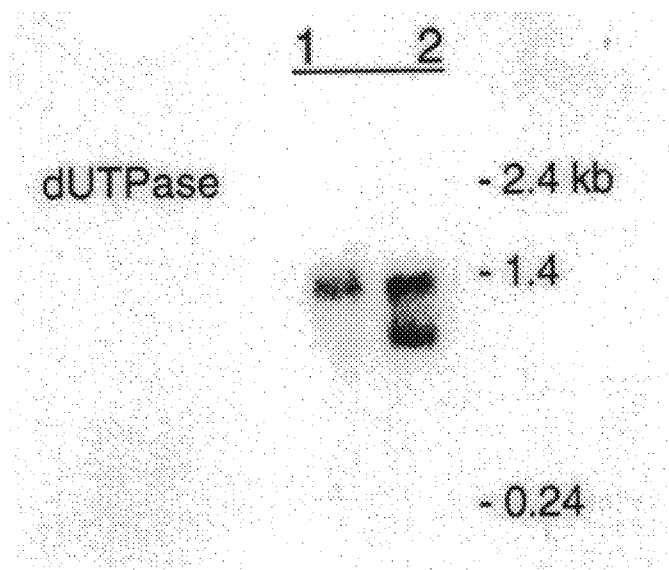
FIG. 15 shows Northern blot analysis of dUTPase in serum starved and serum stimulated 34LU human lung fibroblasts. Poly (A)+RNA was isolated from serum starved and serum stimulated 34 Lu cells, fractionated by agarose gel electrophoresis, and transferred to nitrocellulose for subsequent Northern hybridization analysis. A. The 3' region of the DUT-N cDNA (935 bp SphI/EcoRI fragment), sequence shared between both DUT-N and DUT-M, was used as a probe for hybridization analysis. Lane 1, mRNA isolated from cells serum starved for 72 h. Lane 2, mRNA isolated from cells serum stimulated for 30 h. B. To assure equal loading of mRNA sample, the blot seen in panel A was stripped and reprobed with GAPDH.
Figure 15B:
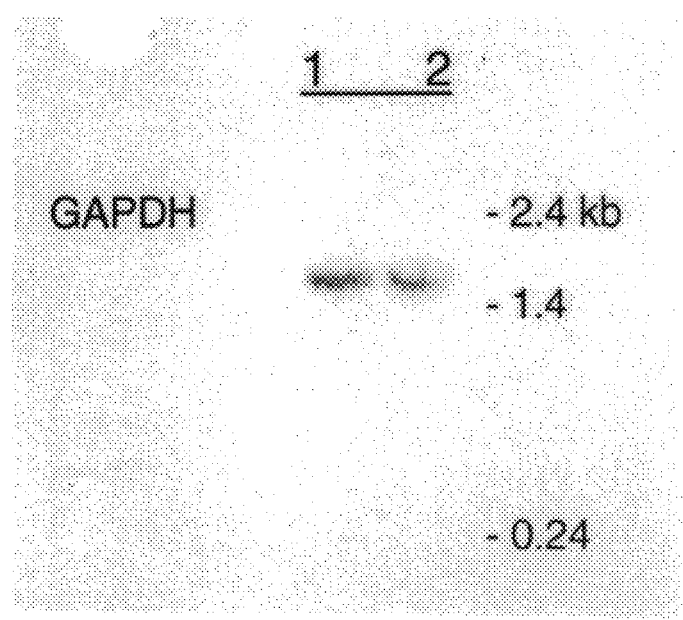

To demonstrate the similar regulatory phenomenon at the mRNA level, Northern blot analysis was performed on mRNA derived from serum-stimulated and serum-starved 34 Lu cells. Cells were either serum starved for 72 hours or serum stimulated for 36 hours and poly (A)$^+$ RNA was isolated. The RNA was fractionated by agarose gel electrophoresis and then transferred to nitrocellulose. The resulting Northern blots were probed with the 3' end (935 bp SphI/EcoRI fragment) of the DUT-N cDNA, a region shared between both isoforms (FIG. 15A). To ensure equal loading of mRNA samples, a GAPDH cDNA was used to probe the identical blot (FIG. 15B). FIG. 8A, lane 1 contains dUTPase mRNA isolated from serum-starved cells and lane 2 contains dUTPase mRNA isolated from serum-stimulated cells. In serum-starved cells (lane 1), a single 1.4 kb dUTPase transcript is evident. Upon serum-stimulation however, a 1.1 kb message is induced, while the levels of the 1.4 kb transcript, observed in quiescent cells, remain the same (lane 2). This pattern of dUTPase mRNA expression mimics dUTPase protein isoform expression, with the inducible 1.1 kb transcript corresponding to DUT-N and the constitutive 1.4 kb transcript corresponding to DUT-M.

Figure 16:
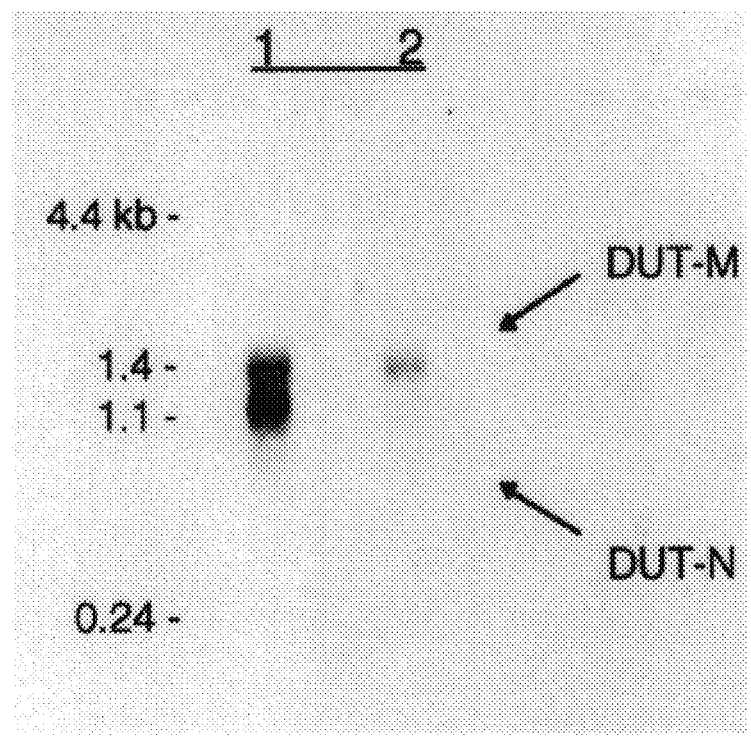
FIG. 16 shows Northern blot analysis of 34 Lu mRNA with a DUT-M-specific probe. Poly (A)+ RNA was isolated from cycling 34 Lu cells, fractionated by agarose gel electrophoresis and transferred to nitrocellulose. Hybridization analysis was performed with either a probe common to both DUT-N and DUT-M (Lane 1) or a probe specific for DUT-M isoform (Lane 2).

To clearly demonstrate the identity of the transcripts, an isoform specific probe was utilized for Northern blot analysis. The extreme 5' end of the DUT-M cDNA sequence is unique, providing for an isoform specific probe. This 5' DUT-M-specific sequence (250 bp EcoRI/AluI fragment) was used to probe 34 Lu mRNA isolated from cycling cells. The common probe (935 bp SphI/EcoRI fragment) was used as a control on an identical blot (FIG. 16). As previously shown, the common probe hybridizes to both the 1.1 and 1.4 kb dUTPase transcripts (FIG. 16, lane 1). The DUT-M specific probe however, specifically hybridizes to the 1.4 kb transcript, indicating that the 1.4 kb transcript encodes DUT-M. Together, these data indicate that the DUT-N and DUT-M isoforms are transcribed as distinct mRNAs of 1.1 and 1.4 kb respectively in 34 Lu cells. In addition, the 1.1 kb transcript is induced as a consequence of serum stimulation while the 1.4 kb, DUT-M transcript is maintained at constant levels regardless of cell growth status.

EXAMPLE 11

N-Terminal Sequence Analysis

Samples of purified HeLa S3 dUTPase were fractionated by 15% SDS-PAGE and transferred onto poly(vinylidene difluoride) (PVDF) membranes (Immobilon P, Millipore). The PVDF membrane was stained with 0.5% Coomassie R250, 20% methanol and 0.5% acetic acid for 1 min and destained in 30% methanol for 5 min. The individual protein bands were cut out and subjected to Edman degradation. Sequence analysis was performed on an Applied Biosystems 470A gas-phase protein sequencer equipped with a Beckman 126/166 system for on-line PTH analysis. Data was acquired using System Gold chromatography software. PVDF membrane samples were loaded directly onto Polybrene coated GF/C filters (ABI) and standard ABI sequencing cycles were used.

EXAMPLE 12

Phosphorylation of Ser-11 of DUT-N

Figure 17:
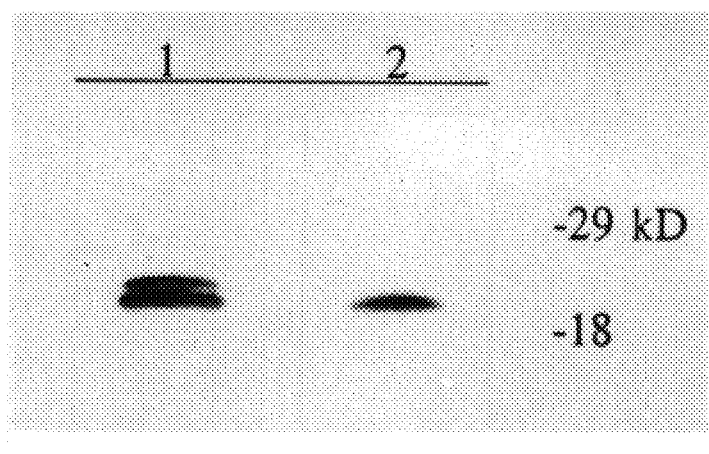
FIG. 17 shows the detection of phosphorylation of DUT-N and the lack of detection of phosphorylation of DUT-M.

HeLa cells were labelled with [$^{32}$p] orthophosphate and dUTPase immunoprecipitated from total cell extracts. The immunoprecipitates were fractionated by 15% SDS-PAGE and subjected to western blot analysis. The immunoblot shown in FIG. 17, lane 1, demonstrates the presence of both DUT-N and DUT-M isoforms. After quenching the chemiluminescent immunoblot reaction, the nitrocellulose membrane was exposed to x-ray film to detect [$^{32}$p] orthophosphate labelling. As seen in FIG. 17, lane 2, all of the radioactivity is associated with the nuclear form of dUTPase (DUT-N) and not the mitochondrially associated species (DUT-M).

HeLa cells were radiolabelled with $^{32}$P-orthophosphate and dUTPase protein was purified by immuno-affinity chromatography. Purified $^{32}$P-labelled dUTPase was fractionated by 15% SDS-PAGE, the protein band corresponding to DUT-N cut out, subjected to tryptic digestion and fractionated by reversed-phase HPLC. A single peak of radioactivity was resolved at 23.5 min during a linear acetonitrile gradient. The phosphopeptide was refractionated and subjected to mass spectrometry analysis.

Figure 18:
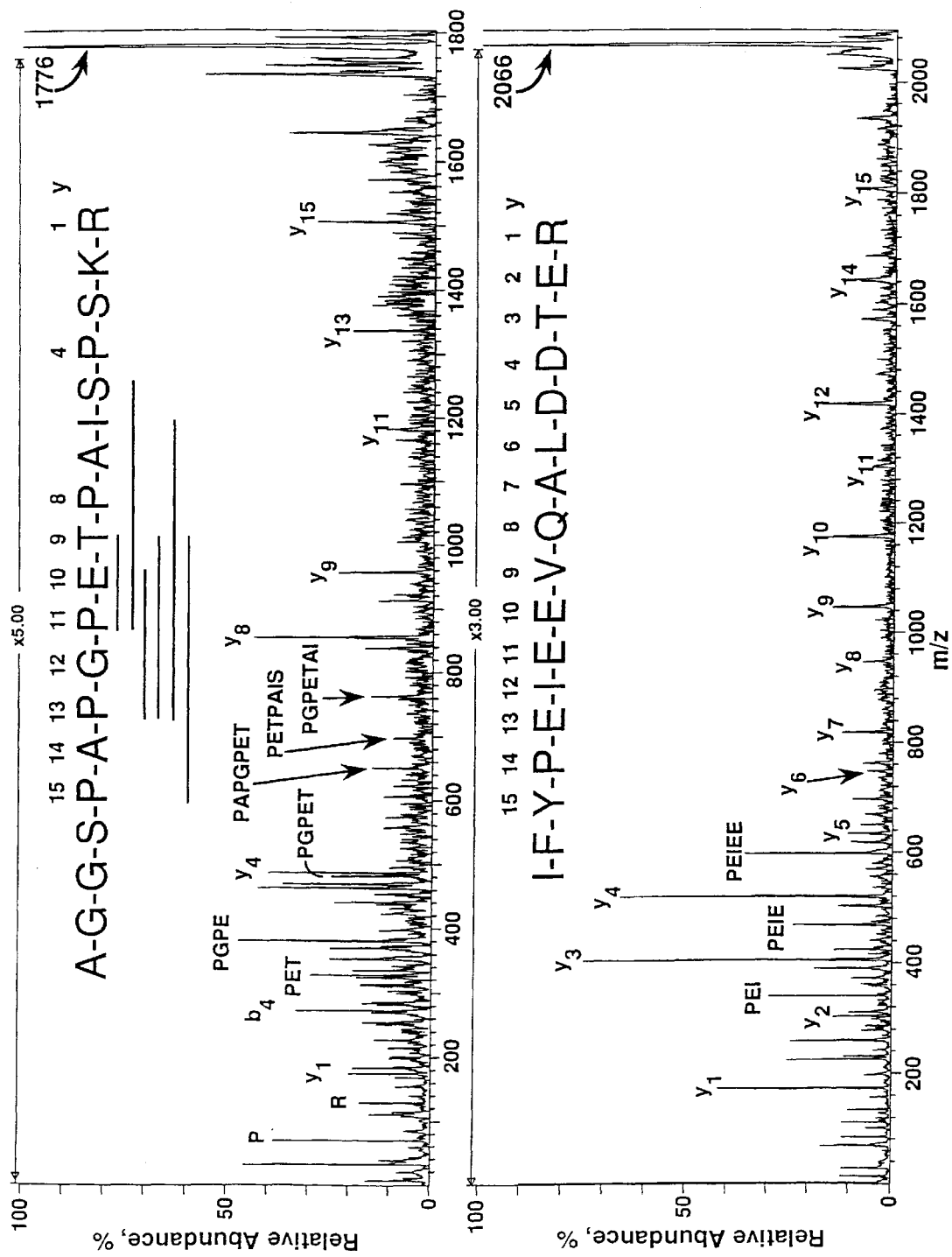
FIG. 18 shows mass spectroscopy analysis of the DUTN phosphopeptide [SEQ ID NO: 20].

The number of phosphate groups and their sequence locations in the phosphopeptide present in the major radioactive fraction was established by electrospray mass spectrometry (Climie et al., Protein Exp. Purif., 5:252–258 (1994), Cedergren-Zeppezauer, et al., Nature, 355:740–743 (1992), Roepstorff and Fohlman, Biomed. Mass Spectrom., 11:60 (1984), each of which is incorporated by reference). See FIG. 18. The major peptide signal observed had a determined $M_r$ of 1638.0. Tandem mass spectrometry (Roepstorff and Fohlman) of the $(M+2H)^{2+}$ parent ion of the phosphorylated peptide provided the partial sequence P-C-S-E-E-T-P-A-X-pS-P- where pS is phospho-Ser, Cys is carboxamidomethylated, and X is either Leu or Ile. This subsequence corresponds to residues 2 to 12 of the mature DUT-N protein. Seq. ID No. 2.

In order to confirm the identity of the serine phosphorylation site, Ser-11 was changed to Ala by site directed mutagenesis. The Ser-11 to Ala mutation was introduced into the dUTPase cDNA using the Transformer Mutagenesis Kit from Clonetech. Nucleotide 82 of the DUT-N cDNA sequence ways changed from C to G utilizing the following mutagenic primer: 5'-TTACTGGGTGCAATGGCGGGT-3'. (Seq. ID No. 18) The mutation was confirmed by sequence analysis.

The wild type DUT-N coding region and the Ser-11→Ala mutant were cloned into the eukaryotic expression vector pEUK-C1 and both constructs were individually transfected into COS 7 cells. After 60 hours, the transfected COS 7 cells were harvested and cell extracts analyzed by immunoblot analysis (FIG. 19A). Expression of both the wild type and mutant dUTPase is evident (FIG. 19A, lanes 2 and 3) while there is no expression from the negative control (vector containing no insert) (FIG. 19A, lane 1).

To further confirm that Ser-11 is the site of DUT-N phosphorylation, transfected cells were labelled with [$^{32}$P] orthophosphate for 10 hours at 50 to 60 hours post-transfection. At 60 h, cells were harvested and extracts prepared. Each sample was subjected to immunoprecipitation analysis using a human dUTPase specific monoclonal antibody. The immunoprecipitates were resolved by 15% SDS-PAGE and visualized by autoradiography. The wild type DUT-N protein is readily phosphorylated in COS 7 cells (FIG. 19B, lane 2). Phosphorylation of the mutant DUT-N however, is blocked by the Ser-11→Ala mutation (FIG. 19B, lane 3). These data further indicate that Ser-11 is the sole phosphorylation site of the nuclear form of human dUTPase in vivo.

Although DUT-N and DUT-M differ in their N-termini, the site of Ser phosphorylation is retained in both isoforms. Despite this conservation, only the DUT-N isoform is phosphorylated in vivo at any detectable levels. Mass spectrometry analysis of the analogous tryptic peptide derived from DUT-M shows no change in mass indicative of a phosphorylated residue.

EXAMPLE 13

Preparation of Peripheral Blood Lymphocytes

HeLa S3 cells (CCL 2.2) were purchased from American Type Culture Collection and maintained in Dulbecco's modified Eagle's medium supplemented with 5% fetal calf serum purchased from GIBCO-BRL. Human peripheral blood lymphocytes (PBLs) were prepared from venous whole blood with LeucoPREP cell separation tubes (Becton Dickinson) using the manufacturer's recommendations. PBLs were cultured in RPMI 1640 medium supplemented with 10% fetal bovine serum. PBLs were stimulated by the addition of phytohemagglutinin (PHA) to a final concentration of 15 µg/ml (SIGMA). The onset of DNA replication was monitored in stimulated PBLs by [$^3$H] thymidine incorporation. At 12 hour intervals after PHA stimulation, cells were labeled for 30 min with 10 µl of [$^3$H] thymidine (1 m/Ci/ml).

EXAMPLE 14

Immunohistochemistry dUTPase and Ki-67 proteins were detected in routine formalin fixed and paraffin embedded tissues utilizing their corresponding mAbs. dUTPase specific monoclonal antibodies (mAb 145.1.2) were generated and prepared as described. These antibodies were used for immunohistochemistry experiments at a dilution of 1:200. Antibodies against the proliferation marker Ki-67 (MIB-1 clone) were purchased from DAKO and used at a dilution of 1:60. dUTPase specific polyclonal antibodies were raised against recombinant DUT-N protein (expressed in the baculovirus system). The polyclonal antibodies were purified by immunoaffinity chromatography and used for immunoblot analysis at a dilution of 1:1000. Enzyme assays were performed as described in Caradonna and Adamkiewicz.

FIG. 10A illustrates a time course experiment where protein extracts from equivalent numbers of PBLs were fractioned by 15% SDS-PAGE and dUTPase detected by Western blot analysis. Time points were taken at 24, 36 and 48 hour post-PHA stimulation, including negative controls. The untreated sample at 24 hours demonstrates that only the higher molecular weight DUT-M isoform is detectable in resting PBLs. In contrast, the sample treated with PHA for 24 hours shows rapid and pronounced expression of the DUT-N isoform in response to the mitogen. The 36 and 48 hour time points show the identical pattern with additional accumulation of the DUT-N isoform in PHA treated cells as a function of time. The induction of the DUT-N protein is estimated to be several hundred-fold, ranging from undetectable levels in resting PBLs to over the linear detection limits of X-ray film after cells were stimulated with PHA for 48 hours.

To determine if the induction of the DUT-N protein is associated with the accumulation of functional enzyme, each sample was assayed for dUTP hydrolyzing activity. As shown in FIG. 10B, the increase in dUTPase protein correlates with increased enzymatic activity suggesting that the newly translated protein is functionally active.

To determine when the induction of the DUT-N protein occurs with respect to the cell cycle, the onset of DNA replication was determined by measuring $^3$H-thymidine incorporation. As seen in FIG. 10C, detectable tritium incorporation begins around 24 hours and increases through 48 hours post stimulation with PHA. DUT-N levels rise just prior to the onset of replication and it is estimated that the induction of the DUT-N protein coincides with mid to late G1 phase.

Primary mAb incubations were performed at room temperature for 45 min. Subsequently, mAbs were detected using an ABC-peroxidase technique in a capillary gap system using detection reagents purchased from BioTek Solutions (Santa Barbara, Calif.). A steam pre-treatment method (BioTek Solutions) enhanced immunohistochemical labeling for both dUTPase and Ki-67 mAbs.

EXAMPLE 15

Immunohistochemical Localization of dUTPase in Normal Human Tissues

The mAb (145.1.2) of Example 9 was used to detect dUTPase in formalin-fixed paraffin embedded human tissues using immunohistochemistry techniques described above. The specificity of this antibody is demonstrated by its ability to immunoprecipitate and immunopurify both DUT-N and DUT-M. In addition, pre-incubation with purified antigen neutralized the reactivity during immunohistochemical detection.

Immunohistochemical staining was performed by the avidin-biotin complex (ABC) technique as described by Haerslev and Jacobsen, APMIS, 102:395–400 (1994), incorporated herein by reference. Immunohistochemical staining of dUTPase in a variety of normal tissues demonstrates intense nuclear staining in highly proliferative tissues such as the replicative cells of the lymphatic system and the basal layer of epithelia. FIG. 4A illustrates intense nuclear staining by the dUTPase mAb in proliferative germinal centers and basal layer epithelium of normal human tonsil.

Serial section of normal human tonsil were stained for the proliferation marker Ki-67 (MIB-1) and dUTPase individually. FIGS. 7B and 7C demonstrate the similar staining of the germinal center region by dUTPase and Ki-67, respectively. Immunohistochemical data demonstrating nuclear staining of dUTPase in proliferative human tissues in consistent with the observation that DUT-N protein is expressed upon mitogenic activation of PBLs in culture.

Diffuse but detectable cytoplasmic staining, independent of the proliferation status, is evident in many normal tissues types. mAb specific for dUTPase cross-reacts with both the DUT-N and DUT-M isoforms. The diffuse cytoplasmic staining observed in various normal tissues represents the mitochondrial isoform which is expressed at much lower levels than DUT-N in replicating cells (FIG. 10A). Cytoplasmic staining of dUTPase observed in tissues regardless of proliferation status is in agreement with the data presented on the cell culture model of dUTPase expression, where expression of the DUT-M isoform occurs independent of proliferation status (FIG. 10A).

EXAMPLE 16

Immunohistochemical Localization of dUTPase in Normal Non-Human Tissues dUTPase is isolated and purified from bovine peripheral lymphocytes by the method described in Example 1. A monoclonal antibody specific for bovine dUTPase is produced by standard methods. dUTPase is detected in formalin fixed and paraffin embedded bovine tissues, such as proliferating tissues such as epidermis and gastrointestinal tissue and in non-proliferating tissues such as kidney, by the method of Examples 11 and 12. Results are similar to those achieved for human tissues.

dUTPase is isolated and purified from frog peripheral lymphocytes by the method described in Example 1. A monoclonal antibody specific for frog dUTPase is produced by standard methods. dUTPase is detected in formalin fixed and paraffin embedded frog, such as proliferating tissues such as epidermis and gastrointestinal tissue and in non-proliferating tissues such as kidney, by the method of Examples 14 and 15. Results are similar to those achieved for bovine and human tissues.

EXAMPLE 17

Immunohistochemical Detection of dUTPase in Neoplastic Tissues

To demonstrate the utility of dUTPase as a proliferation marker useful for cancer evaluation, neoplastic tissues were stained for dUTPase and Ki-67 to compare the expression of these proteins. See FIGS. 8 and 9. There was strong correlation between nuclear dUTPase staining and highly proliferative tumors as judged by similar staining with Ki-67. FIG. 6 shows an example of the specific nuclear localization of dUTPase staining in a metastatic adenocarcinoma. A serial section of the same tumor was also strongly positive for Ki-67.

In Ki-67 negative neoplasms, a different staining pattern is observed. All of the Ki-67 negative neoplasms investigated were negative for nuclear dUTPase staining, a result consistent with observations in normal tissues. However, a specific subset of the cancers surveyed demonstrated intense cytoplasmic staining of dUTPase, far above the cytoplasmic staining observed in normal human tissues. FIG. 9 shows a Ki-67 negative, well differentiated, infiltrative ductal carcinoma of the breast stained for dUTPase. Intense cytoplasmic staining is observed in the neoplastic ductal cells. This intense cytoplasmic staining is useful for identifying specific neoplastic phenotypes in Ki-67 negative tumors.

EXAMPLE 18

Immunohistochemical Detection of dUTPase in Non-human Neoplastic Tissues

Various canine, feline, bovine, equine, mouse, guinea pig, and frog neoplasms are stained for dUTPase as described in Example 17. Results are similar to those obtained in human neoplastic tissues.

The references cited in this specification are incorporated herein by reference.

It will be understood that many variations can be made in the procedures herein described for the use of dUTPase to determine the proliferative status of a cell or a tissue while still remaining within the bounds of the present invention. Likewise, it is understood that, due to the degeneracy of the genetic code, nucleic acid sequences with codons equivalent to those disclosed will encode functionally equivalent or identical proteins as disclosed herein. It is the intention of the inventors that such variations are included within the scope of the invention.

---

What is claimed is:

1. An isolated protein comprising an amino acid sequence selected from those shown in SEQ ID NO:2 and SEQ ID NO:4, which sequences are the nuclear and mitochondrial form of human dUTPase, respectively, which isolated protein is essentially free of HeLa cell proteins.

2. The isolated protein of claim 1 which has the amino acid sequence shown in Seq. ID No. 2, which protein is the nuclear form of human dUTPase.

3. The isolated protein of claim 1 which has the amino acid sequence shown in Seq. ID No. 4, which protein is the mitochondrial form of human dUTPase.

4. The isolated protein of claim 3, which is a recombinantly produced protein.

5. The isolated nuclear dUTPase protein of claim 2, which is a recombinantly produced protein.

6. An isolated protein comprising a nuclear form of human dUTPase which protein has a phosphorylation site at a serine residue within 31 amino acids from the amino terminal of the protein but is essentially free of phosphorylations at this serine.

7. The isolated nuclear dUTPase protein of claim 6, which is a recombinantly produced protein.

8. A kit comprising an isolated nuclear form of human dUTPase and an isolated mitochondrial form of human dUTPase, which proteins are essentially free of phosphorylations at serine residues.

9. The kit of claim 8, wherein the nuclear form of human dUTPase has the amino acid sequence shown in SEQ. ID NO:2.

10. The kit of claim 8, wherein the mitochondrial form of human dUTPase has the amino acid sequence shown in SEQ. ID NO:4.

11. The isolated protein of claim 6, which comprises the amino acid sequence shown in SEQ ID NO:2 which protein is the nuclear form of human dUTPase.

12. The isolated protein of claim 6, which comprises the amino acid sequence shown in SEQ ID NO:4 which protein is the mitochondrial form of human dUTPase.

13. An isolated, purified, recombinant protein which sequence is the mitochondrial form of human dUTPase.

14. The isolated protein of claim 13, wherein the protein has amino acid sequence that comprises that shown in SEQ ID NO:4.

\* \* \* \* \*

UNITED STATES PATENT AND TRADEMARK OFFICE
CERTIFICATE OF CORRECTION

PATENT NO.   : 5,962,246
DATED        : October 5, 1999
INVENTOR(S)  : Robert D. Ladner et al.

It is certified that error appears in the above-identified patent and that said Letters Patent is hereby corrected as shown below:

<u>Column 1,</u>
Line 9, before "FIELD OF THE INVENTION," insert the following paragraph:

-- STATEMENT REGARDING FEDERALLY SPONSORED RESEARCH OR DEVELOPMENT

This invention was made with government support under Grant No. CA42605 awarded by National Institutes of Health. The Government has certain rights in the invention. --

Signed and Sealed this

First Day of July, 2003

JAMES E. ROGAN
*Director of the United States Patent and Trademark Office*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
        (A) LENGTH: 1037 base pairs
        (B) TYPE: nucleic acid
        (C) STRANDEDNESS: double
        (D) TOPOLOGY: linear (xi) SEQUENCE DESCRIPTION: SEQ ID NO:1:

```
CGTCTCCTCG CTCGCCTTCT GGCTCTGCCA TGCCCTGCTC TGAAGAGACA CCCGCCATTT      60

CACCCAGTAA GCGGGCCCGG CCTGCGGAGG TGGGCGGCAT GCAGCTCCGC TTTGCCCGGC     120

TCTCCGAGCA CGCCACGGCC CCCACCCGGG GCTCCGCGCG CGCCGCGGGC TACGACCTGT     180

ACAGTGCCTA TGATTACACA ATACCACCTA TGGAGAAAGC TGTTGTGAAA ACGGACATTC     240

AGATAGCGCT CCCTTCTGGG TGTTATGGAA GAGTGGCTCC ACGGTCAGGC TTGGCTGCAA     300

AACACTTTAT TGATGTAGGA GCTGGTGTCA TAGATGAAGA TTATAGAGGA AATGTTGGTG     360

TTGTACTGTT TAATTTTGGC AAAGAAAAGT TTGAAGTCAA AAAAGGTGAT CGAATTGCAC     420

AGCTCATTTG CGAACGGATT TTTTATCCAG AAATAGAAGA AGTTCAAGCC TTGGATGACA     480

CCGAAAGGGG TTCAGGAGGT TTTGGTTCCA CTGGAAAGAA TTAAAATTTA TGCCAAGAAC     540

AGAAAACAAG AAGTCATACC TTTTTCTTAA AAAAAAAAAA AGTTTTTGCT TCAAGTGTTT     600

TGGTGTTTTG CACTTCTGTA AACTTACTAG CTTTACCTTC TAAAAGTACT GCATTTTTTA     660

CTTTTTTTTA TGATCAAGGA AAAGATCATT AAAAAAAAAC ACAAAGAAG TTTTTCTTTG      720

TGTTTGGATC AAAAAGAAAC TTTGTTTTTC CGCAATTGAA GGTTGTATGT AAATCTGCTT     780

TGTGGTGACC TGATGTAAAC AGTGTCTTCT TAAAATCAAA TGTAAATCAA TTACAGATTA     840

AAAAAAAAAA GCCTGTATTT AACTCATATG ATCTCCCTTC AGCAACTTAT TTTGCTTTAA     900

TTGCTTTAAA TCTTAAGCAA TATTTTTTAT TCAGTAAACA AATTCTTTCA CAAGGTACAA     960

AATCTTGCAT AAGCTGAACT AAAATAAAAA TGAAAAGGAG AGATTAAAAA AAAAAAAAAA    1020

AAAAAAAAAA AAAAAAA                                                  1037
```

(2) INFORMATION FOR SEQ ID NO:2:

(i) SEQUENCE CHARACTERISTICS:
        (A) LENGTH: 164 amino acids
        (B) TYPE: amino acid
        (C) STRANDEDNESS: single
        (D) TOPOLOGY: linear (xi) SEQUENCE DESCRIPTION: SEQ ID NO:2:

```
Met Pro Cys Ser Glu Glu Thr Pro Ala Ile Ser Pro Ser Lys Arg Ala
 1               5                  10                  15

Arg Pro Ala Glu Val Gly Gly Met Gln Leu Arg Phe Ala Arg Leu Ser
            20                  25                  30
```

Glu His Ala Thr Ala Pro Thr Arg Gly Ser Ala Arg Ala Ala Gly Tyr
     35                  40                  45

Asp Leu Tyr Ser Ala Tyr Asp Tyr Thr Ile Pro Pro Met Glu Lys Ala
 50                  55                  60

Val Val Lys Thr Asp Ile Gln Ile Ala Leu Pro Ser Gly Cys Tyr Gly
65                  70                  75                  80

Arg Val Ala Pro Arg Ser Gly Leu Ala Ala Lys His Phe Ile Asp Val
                 85                  90                  95

Gly Ala Gly Val Ile Asp Glu Asp Tyr Arg Gly Asn Val Gly Val Val
                100                 105                 110

Leu Phe Asn Phe Gly Lys Glu Lys Phe Glu Val Lys Lys Gly Asp Arg
            115                 120                 125

Ile Ala Gln Leu Ile Cys Glu Arg Ile Phe Tyr Pro Glu Ile Glu Glu
        130                 135                 140

Val Gln Ala Leu Asp Asp Thr Glu Arg Gly Ser Gly Gly Phe Gly Ser
145                 150                 155                 160

Thr Gly Lys Asn (2) INFORMATION FOR SEQ ID NO:3:

(i) SEQUENCE CHARACTERISTICS:
        (A) LENGTH: 960 base pairs
        (B) TYPE: nucleic acid
        (C) STRANDEDNESS: double
        (D) TOPOLOGY: linear (xi) SEQUENCE DESCRIPTION: SEQ ID NO:3:

```
GGTGGAAGCC TGGCGCACGT CCGGAGGTGC CGAGGACCCA ACCAGCCCAA ACTCTGGGGG      60

AAATGACTCC CCTCTGCCCT CGCCCCGCGC TCTGCTACCA TTTCCTTACG TCTCTGCTTC     120

GCTCAGCGAT GCAAAACGCG CGAGGCACGG CAGAGGGCCG AAGCCGCGGT ACTCTCCGGG     180

CCAGGCCCGC CCCTCGGCCG CCGGCGGCGC AGCACGGGAT TCCCCGGCCG CTGTCCAGCG     240

CTGGCCGCCT GAGCCAAGGC TGCCGCGGAG CCAGTACAGT CGGGGCCGCT GGCTGGAAGG     300

GCGAGCTTCC TAAGGCGGGG GGAAGCCCGG CGCCGGGGCC GGAGACACCC GCCATTTCAC     360

CCAGTAAGCG GGCCCGGCCT GCGGAGGTGG GCGGCATGCA GCTCCGCTTT GCCCGGCTCT     420

CCGAGCACGC CACGGCCCCC ACCCGGGGCT CCGCGCGCGC CGCGGGCTAC GACCTGTACA     480

GTGCCTATGA TTACACAATA CCACCTATGG AGAAAGCTGT TGTGAAAACG GACATTCAGA     540

TAGCGCTCCC TTCTGGGTGT TATGGAAGAG TGGCTCCACG GTCAGGCTTG GCTGCAAAAC     600

ACTTTATTGA TGTAGGAGCT GGTGTCATAG ATGAAGATTA TAGAGGAAAT GTTGGTGTTG     660

TACTGTTTAA TTTTGGCAAA GAAAAGTTTG AAGTCAAAAA AGGTGATCGA ATTGCACAGC     720

TCATTTGCGA ACGGATTTTT TATCCAGAAA TAGAAGAAGT TCAAGCCTTG GATGACACCG     780

AAAGGGGTTC AGGAGGTTTT GGTTCCACTG GAAAGAATTA AAATTTATGC CAAGAACAGA     840

AAACAAGAAG TCATACCTTT TTCTTAAAAA AAAAAAAAGT TTTTGCTTCA AGTGTTTTGG     900

TGTTTTGCAC TTCTGTAAAC TTACTAGCTT TACCTTCTAA AAGTACTGCA TTTTTTACTT     960
```

(2) INFORMATION FOR SEQ ID NO:4:

(i) SEQUENCE CHARACTERISTICS:
        (A) LENGTH: 252 amino acids
        (B) TYPE: amino acid
        (C) STRANDEDNESS: single
        (D) TOPOLOGY: linear (xi) SEQUENCE DESCRIPTION: SEQ ID NO:4:

| Met | Thr | Pro | Leu | Cys | Pro | Arg | Pro | Ala | Leu | Cys | Tyr | His | Phe | Leu | Thr |
| 1 | | | | 5 | | | | | 10 | | | | | 15 | |

| Ser | Leu | Leu | Arg | Ser | Ala | Met | Gln | Asn | Ala | Arg | Gly | Thr | Ala | Glu | Gly |
| | | | | 20 | | | | | 25 | | | | | 30 | |

| Arg | Ser | Arg | Gly | Thr | Leu | Arg | Ala | Arg | Pro | Ala | Pro | Arg | Pro | Pro | Ala |
| | | | | 35 | | | | | 40 | | | | | 45 | |

| Ala | Gln | His | Gly | Ile | Pro | Arg | Pro | Leu | Ser | Ser | Ala | Gly | Arg | Leu | Ser |
| | 50 | | | | | 55 | | | | | 60 | | | | |

| Gln | Gly | Cys | Arg | Gly | Ala | Ser | Thr | Val | Gly | Ala | Ala | Gly | Trp | Lys | Gly |
| 65 | | | | | 70 | | | | | 75 | | | | | 80 |

| Glu | Leu | Pro | Lys | Ala | Gly | Gly | Ser | Pro | Ala | Pro | Gly | Pro | Glu | Thr | Pro |
| | | | | 85 | | | | | 90 | | | | | 95 | |

| Ala | Ile | Ser | Pro | Ser | Lys | Arg | Ala | Arg | Pro | Ala | Glu | Val | Gly | Gly | Met |
| | | | | 100 | | | | | 105 | | | | | 110 | |

| Gln | Leu | Arg | Phe | Ala | Arg | Leu | Ser | Glu | His | Ala | Thr | Ala | Pro | Thr | Arg |
| | | | | 115 | | | | | 120 | | | | | 125 | |

| Gly | Ser | Ala | Arg | Ala | Ala | Gly | Tyr | Asp | Leu | Tyr | Ser | Ala | Tyr | Asp | Tyr |
| | 130 | | | | | 135 | | | | | 140 | | | | |

| Thr | Ile | Pro | Pro | Met | Glu | Lys | Ala | Val | Val | Lys | Thr | Asp | Ile | Gln | Ile |
| 145 | | | | | 150 | | | | | 155 | | | | | 160 |

| Ala | Leu | Pro | Ser | Gly | Cys | Tyr | Gly | Arg | Val | Ala | Pro | Arg | Ser | Gly | Leu |
| | | | | 165 | | | | | 170 | | | | | 175 | |

| Ala | Ala | Lys | His | Phe | Ile | Asp | Val | Gly | Ala | Gly | Val | Ile | Asp | Glu | Asp |
| | | | | 180 | | | | | 185 | | | | | 190 | |

| Tyr | Arg | Gly | Asn | Val | Gly | Val | Val | Leu | Phe | Asn | Phe | Gly | Lys | Glu | Lys |
| | | | | 195 | | | | | 200 | | | | | 205 | |

| Phe | Glu | Val | Lys | Lys | Gly | Asp | Arg | Ile | Ala | Gln | Leu | Ile | Cys | Glu | Arg |
| | | | | 210 | | | | | 215 | | | | | 220 | |

| Ile | Phe | Tyr | Pro | Glu | Ile | Glu | Glu | Val | Gln | Ala | Leu | Asp | Asp | Thr | Glu |
| 225 | | | | | 230 | | | | | 235 | | | | | 240 |

| Arg | Gly | Ser | Gly | Gly | Phe | Gly | Ser | Thr | Ser | Lys | Asn |
| | | | | 245 | | | | | 250 | | |

(2) INFORMATION FOR SEQ ID NO:5:

(i) SEQUENCE CHARACTERISTICS:
        (A) LENGTH: 1683 base pairs
        (B) TYPE: nucleic acid
        (C) STRANDEDNESS: double
        (D) TOPOLOGY: linear (xi) SEQUENCE DESCRIPTION: SEQ ID NO:5:

```
GATCCTCTAG AGTCGACCTG CAGGTCGACT CTAGAGGATC CTTGTTCGAC TCCTAGCAAG      60
GGGTTCCCAC TGCGTTTCTG TTGGGTTATC CCAAACCTCT GATAGGATAG TAGCGCCCTC     120
CCTGCCTCCG GTCGAATAAA CACTACAACG TCTGACACTC GGTGCTGAAA GGAAATCGGG     180
CGCAATAACT GTCACCGGCG CCGAGATGCG GTTCGGCGCT TAGGCCTAAA CTCAGAGCCC     240
GGGAGTCATG GCTGCCGGGG TGCCGCCCCA GGTAAATCAG TCCAGGCGCA GGGCCCGGGC     300
CTGGCGTACA CTCTCGGAAA AATGGGGGCC AGAGCAAACA AGAAGAGCGA AGCAAGAGG      360
GCTAGGCAGC CAGAGGGCAG AAGACTCAAG ACGCCAACGG CCGTCTTCCT GGGGCCCCAG     420
GGCTGCGCCA TCCCTGGGCT GCCGGGGCAC CGCCTCTCCA CGCCCCTCGT CCGGCGGCGG     480
CTGCGACTGC TTCCGAGGTC ATGTTCCCAG GACGGGCGCG TCTTCAGGGT GGAAGCCTGG     540
CGCACGTCCG GAGGTGCCGA GGACCCAACC AGCCCAAACT CTGGGGGAAA TGACTCCCCT     600
```

```
CTGCCCTCGC CCCGCGCTCT GCTACCATTT CCTTACGTCT CTGCTTCGCT CAGCGATGCA      660

AAACGCGCGA GGCACGGCAG AGGGCCGAAG CCGCGGTACT CTCCGGGCCA GGCCCGCCCC      720

TCGGCCGCCG GCGGCGCAGC ACGGGATTCC CCGGCCGCTG TCCAGCGCTG GCCGCCTGAG      780

CCAAGGCTGC CGCGGAGCCA GTACAGTCGG GGCCGCTGGC TGGAAGGGCG AGCTTCCTAA      840

GGCGGGGGGA AGCCCGGCGC CGGGGCCGGG TAGGAAAGGC GGGGGAGGGG CTCCGGCCGT      900

CTGGAAGGAA TCCACGCGGC TTGAGGCTGT GGGGAAGTAG GGTGGCGAGC GGTGGTTCTG      960

CGCGCGGGGG GCGGGGGGGT GGGGTGGTCC ATTAGGGGCC CCTGGCGAGG GGGCGGCTTT     1020

CTAGTGTGTG AGGCGACGCC CTAGAAGCTC CCCTTCAAAG TTGGCCCCAC GCGCTGAATG     1080

TGGAAAGTTG ACTGGGACCC AGTAGTTTCC CATCCCAAAC CTGCTTTCCG AGAAGGGCTT     1140

CAAACCCAAA ATGTGAATCC CGCCTCCCCT CTCACCAGAA CTGTGGACTC GTCCCGGGGA     1200

GGGGCGGTGG GTGGGGCGGG GCTGGCGGGA AATTTCGGTT TTGGCGCGCT CCCTGCGGCG     1260

ACGCTCATCG TGCGCTCTCC TCTTCCCCCG GTGGTCTCCT CGCTCGCCTT CTGGCTCTGC     1320

CATGCCCTGC TCTGAAGAGA CACCCGCCAT TTCACCCAGT AAGCGGGCCC GGCCTGCGGA     1380

GGTGGGCGGC ATGCAGCTCC GCTTTGCCCG GCTCTCCGAG CACGCCACGG CCCCCACCCG     1440

GGGCTCCGCG CGCGCCGCGG GCTACGACCT GTACAGGTGA GCGGGACCT GCCGGCGAGG     1500

AGGCTGGGAA GGGCCGGCCG TCCGCTGCCA CAGCTAGAAA CAGTCACCGG AGAGATCACA     1560

GGAACACAGT AGCTATGGGT AGGATTTCTG CCTTTTTCGT GTTTAAAATT TTAGCTTTCA     1620

TCTTTGGCAT AAACCAAATA GAGATTTGGG CAAAGACTGC AGAATAAGTA AAATAGCTAT     1680

ACC                                                                 1683

(2) INFORMATION FOR SEQ ID NO:6:

(i) SEQUENCE CHARACTERISTICS:
        (A) LENGTH: 147 amino acids
        (B) TYPE: amino acid
        (C) STRANDEDNESS: single
        (D) TOPOLOGY: linear (xi) SEQUENCE DESCRIPTION: SEQ ID NO:6:

Met Thr Ala Thr Ser Asp Lys Val Leu Asn Ile Gln Leu Arg Ser Ala
 1               5                  10                  15

Ser Ala Thr Val Pro Thr Lys Gly Ser Ala Thr Ala Gly Tyr Asp
                20                  25                  30

Ile Tyr Ala Ser Gln Asp Ile Thr Ile Pro Ala Met Gly Gln Gly Met
            35                  40                  45

Val Ser Thr Asp Ile Ser Phe Thr Val Pro Val Gly Thr Tyr Gly Arg
 50                  55                  60

Ile Ala Pro Arg Ser Gly Leu Ala Val Lys Asn Gly Ile Gln Thr Gly
65                  70                  75                  80

Ala Gly Val Val Asp Arg Asp Tyr Thr Gly Glu Val Lys Val Val Val
                85                  90                  95

Phe Asn His Ser Gln Arg Asp Phe Ala Ile Lys Lys Gly Asp Arg Val
            100                 105                 110

Ala Gln Leu Ile Leu Glu Lys Ile Val Asp Asp Ala Gln Ile Val Val
        115                 120                 125

Val Asp Ser Leu Glu Glu Ser Ala Arg Gly Arg Gly Phe Gly Ser
    130                 135                 140

Thr Gly Lys
145
```

(2) INFORMATION FOR SEQ ID NO:7:

(i) SEQUENCE CHARACTERISTICS:
        (A) LENGTH: 151 amino acids
        (B) TYPE: amino acid
        (C) STRANDEDNESS: single
        (D) TOPOLOGY: linear (xi) SEQUENCE DESCRIPTION: SEQ ID NO:7:

Met Lys Lys Ile Asp Val Lys Ile Leu Asp Pro Arg Val Gly Lys Glu
1               5                   10                  15

Phe Pro Leu Pro Thr Tyr Ala Thr Ser Gly Ser Ala Gly Leu Asp Leu
                20                  25                  30

Arg Ala Cys Leu Asn Asp Ala Val Glu Leu Ala Pro Gly Asp Thr Thr
            35                  40                  45

Leu Val Pro Thr Gly Leu Ala Ile His Ile Ala Asp Pro Ser Leu Ala
        50                  55                  60

Ala Met Met Leu Pro Arg Ser Gly Leu Gly His Lys His Gly Ile Val
65                  70                  75                  80

Leu Gly Asn Leu Val Gly Leu Ile Asp Ser Asp Tyr Gln Gly Gln Leu
                85                  90                  95

Met Ile Ser Val Trp Asn Arg Gly Gln Asp Ser Phe Thr Ile Gln Pro
                100                 105                 110

Gly Glu Arg Ile Ala Gln Met Ile Phe Val Pro Val Val Gln Ala Glu
                115                 120                 125

Phe Asn Leu Val Glu Asp Phe Asp Ala Thr Asp Arg Gly Glu Gly Gly
            130                 135                 140

Phe Gly His Ser Gly Arg Gln
145                 150

(2) INFORMATION FOR SEQ ID NO:8:

(i) SEQUENCE CHARACTERISTICS:
        (A) LENGTH: 141 amino acids
        (B) TYPE: amino acid
        (C) STRANDEDNESS: single
        (D) TOPOLOGY: linear (xi) SEQUENCE DESCRIPTION: SEQ ID NO:8:

Ser Leu Trp Gly Gly Gln Leu Cys Ser Ser Gln Gln Lys Gln Pro Ile
1               5                   10                  15

Ser Lys Leu Thr Arg Ala Thr Pro Gly Ser Ala Gly Leu Asp Leu Ser
                20                  25                  30

Ser Thr Ser His Thr Val Leu Thr Pro Glu Met Gly Pro Gln Ala Leu
            35                  40                  45

Ser Thr Gly Ile Tyr Pro Gly Leu Pro Pro Asn Thr Phe Gly Leu Ile
        50                  55                  60

Leu Gly Arg Ser Ser Ile Thr Ile Lys Gly Leu Gln Val Tyr Pro Gly
65                  70                  75                  80

Val Ile Asp Asn Asp Tyr Thr Gly Glu Ile Lys Ile Met Ala Lys Ala
                85                  90                  95

Val Asn Asn Ile Val Thr Val Pro Gln Gly Asn Arg Ile Ala Gln Leu
                100                 105                 110

Ile Leu Leu Pro Leu Ile Glu Thr Asp Asn Lys Val Gln Gln Pro Tyr
            115                 120                 125

Arg Gly Gln Gly Ser Phe Gly Ser Ser Asp Ile Tyr Trp
        130                 135                 140

(2) INFORMATION FOR SEQ ID NO:9:

```
    (i) SEQUENCE CHARACTERISTICS:
        (A) LENGTH: 142 amino acids
        (B) TYPE: amino acid
        (C) STRANDEDNESS: single
        (D) TOPOLOGY: linear (xi) SEQUENCE DESCRIPTION: SEQ ID NO:9:

Gly Val Lys Gly Ser Gly Leu Asn Pro Glu Ala Pro Phe Phe Pro Ile
 1               5                  10                  15

His Asp Leu Pro Arg Gly Thr Pro Gly Ser Ala Gly Leu Asp Leu Ser
                20                  25                  30

Ser Gln Lys Asp Leu Ile Leu Ser Leu Glu Asp Gly Val Ser Leu Val
        35                  40                  45

Pro Thr Leu Val Lys Gly Thr Leu Pro Glu Gly Thr Thr Gly Leu Ile
50                  55                  60

Ile Gly Arg Ser Ser Asn Tyr Lys Lys Gly Leu Glu Val Leu Pro Gly
65                  70                  75                  80

Val Ile Asp Ser Asp Phe Gln Gly Glu Ile Lys Val Met Val Lys Ala
                85                  90                  95

Ala Lys Asn Ala Val Ile Ile His Lys Gly Glu Arg Ile Ala Gln Leu
                100                 105                 110

Leu Leu Leu Pro Tyr Leu Lys Leu Pro Asn Pro Val Ile Lys Glu Glu
        115                 120                 125

Arg Gly Ser Glu Gly Phe Gly Ser Pro Ser His Val His Trp
130                 135                 140

(2) INFORMATION FOR SEQ ID NO:10:

(i) SEQUENCE CHARACTERISTICS:
        (A) LENGTH: 138 amino acids
        (B) TYPE: amino acid
        (C) STRANDEDNESS: single
        (D) TOPOLOGY: linear (xi) SEQUENCE DESCRIPTION: SEQ ID NO:10:

Ser Glu Ile Phe Leu Ala Lys Glu Gly Arg Gly Ile Leu Gln Lys Arg
 1               5                  10                  15

Ala Glu Asp Ala Gly Tyr Asp Leu Ile Cys Pro Gln Glu Ile Ser Ile
                20                  25                  30

Pro Ala Gly Gln Val Lys Arg Ile Ala Ile Asp Leu Lys Ile Asn Leu
        35                  40                  45

Lys Lys Asp Gln Trp Ala Met Ile Gly Thr Lys Ser Ser Phe Ala Asn
50                  55                  60

Lys Gly Val Phe Val Gln Gly Gly Ile Ile Asp Ser Gly Tyr Gln Gly
65                  70                  75                  80

Thr Ile Gln Val Val Ile Tyr Asn Ser Asn Lys Glu Val Val Ile
                85                  90                  95

Pro Gln Gly Arg Lys Phe Ala Gln Leu Ile Leu Met Pro Leu Ile His
                100                 105                 110

Glu Glu Leu Glu Pro Trp Gly Glu Thr Arg Lys Thr Glu Arg Gly Glu
        115                 120                 125

Gln Gly Phe Gly Ser Thr Gly Met Tyr Trp
130                 135

(2) INFORMATION FOR SEQ ID NO:11:

(i) SEQUENCE CHARACTERISTICS:
        (A) LENGTH: 138 amino acids
        (B) TYPE: amino acid
```

(C) STRANDEDNESS: single
(D) TOPOLOGY: linear (xi) SEQUENCE DESCRIPTION: SEQ ID NO:11:

Glu Glu Ile Met Leu Ala Tyr Gln Gly Thr Gln Ile Lys Glu Lys Arg
1               5                   10                  15

Asp Glu Asp Ala Gly Phe Asp Leu Cys Val Pro Tyr Asp Ile Met Ile
                20                  25                  30

Pro Val Ser Asp Thr Lys Ile Ile Pro Thr Asp Val Lys Ile Gln Val
            35                  40                  45

Pro Pro Asn Ser Phe Gly Trp Val Thr Gly Lys Ser Ser Met Ala Lys
50                  55                  60

Gln Gly Leu Leu Ile Asn Gly Gly Ile Ile Asp Glu Gly Tyr Thr Gly
65                  70                  75                  80

Glu Ile Gln Val Ile Cys Thr Asn Ile Gly Lys Ser Asn Ile Lys Leu
                85                  90                  95

Ile Glu Gly Gln Lys Phe Ala Gln Leu Ile Ile Leu Gln His His Ser
                100                 105                 110

Asn Ser Arg Gln Pro Trp Asp Glu Asn Lys Ile Ser Gln Arg Gly Asp
            115                 120                 125

Lys Gly Phe Gly Ser Thr Gly Val Phe Trp
            130                 135

(2) INFORMATION FOR SEQ ID NO:12:

(i) SEQUENCE CHARACTERISTICS:
        (A) LENGTH: 147 amino acids
        (B) TYPE: amino acid
        (C) STRANDEDNESS: single
        (D) TOPOLOGY: linear (xi) SEQUENCE DESCRIPTION: SEQ ID NO:12:

Met Glu Phe Cys His Thr Glu Thr Leu Gln Val Val Arg Leu Ser Gln
1               5                   10                  15

Asn Ala Thr Ile Pro Ala Arg Gly Ser Pro Gly Ala Ala Gly Leu Asp
                20                  25                  30

Leu Cys Ser Ala Tyr Asp Cys Val Ile Pro Ser His Cys Ser Arg Val
            35                  40                  45

Val Phe Thr Asp Leu Leu Ile Lys Pro Pro Ser Gly Cys Tyr Gly Arg
50                  55                  60

Ile Ala Pro Arg Ser Gly Ala Val Lys His Phe Ile Asp Val Gly Ala
65                  70                  75                  80

Gly Val Ile Asp Glu Asp Tyr Arg Gly Asn Val Gly Val Val Leu Phe
                85                  90                  95

Asn Phe Gly Asn Ser Asp Phe Glu Val Lys Lys Gly Asp Arg Ile Ala
                100                 105                 110

Gln Leu Ile Cys Glu Arg Ile Ser Cys Pro Ala Val Gln Glu Val Asn
            115                 120                 125

Cys Leu Asp Asn Thr Asp Arg Gly Asp Ser Gly Phe Gly Ser Thr Gly
            130                 135                 140

Ser Gly Ala
145

(2) INFORMATION FOR SEQ ID NO:13:

(i) SEQUENCE CHARACTERISTICS:
        (A) LENGTH: 144 amino acids
        (B) TYPE: amino acid
        (C) STRANDEDNESS: single (D) TOPOLOGY: linear (xi) SEQUENCE DESCRIPTION: SEQ ID NO:13:

Met Asn Ile Asn Ser Pro Val Arg Phe Val Lys Glu Thr Asn Arg Ala
 1               5                  10                  15

Lys Ser Pro Thr Arg Gln Ser Pro Tyr Ala Ala Gly Tyr Asp Leu Tyr
                20                  25                  30

Ser Ala Tyr Asp Tyr Thr Ile Phe Pro Gly Glu Arg Gln Leu Ile Lys
            35                  40                  45

Thr Asp Ile Ser Met Ser Met Pro Lys Gly Cys Tyr Gly Arg Ile Ala
        50                  55                  60

Pro Arg Ser Gly Leu Ser Leu Lys Gly Ile Asp Ile Gly Gly Gly Val
65                  70                  75                  80

Ile Asp Glu Asp Tyr Arg Gly Asn Ile Gly Val Ile Leu Ile Asn Asn
                85                  90                  95

Gly Lys Cys Thr Phe Asn Val Asn Thr Gly Asp Arg Ile Ala Gln Leu
                100                 105                 110

Ile Tyr Gln Arg Ile Tyr Tyr Pro Glu Leu Glu Glu Val Gln Ser Leu
            115                 120                 125

Asp Ser Thr Asn Arg Gly Asp Gln Gly Phe Gly Ser Thr Gly Leu Arg
        130                 135                 140

(2) INFORMATION FOR SEQ ID NO:14:

(i) SEQUENCE CHARACTERISTICS:
        (A) LENGTH: 184 amino acids
        (B) TYPE: amino acid
        (C) STRANDEDNESS: single
        (D) TOPOLOGY: linear (xi) SEQUENCE DESCRIPTION: SEQ ID NO:14:

Glu Leu Thr Pro Val Gln Thr Glu His Gly Asp Gly Val Arg Glu Ala
 1               5                  10                  15

Ile Ala Phe Leu Pro Lys Arg Glu Glu Asp Ala Gly Phe Asp Ile Val
                20                  25                  30

Val Arg Arg Pro Val Thr Val Pro Ala Asn Gly Thr Thr Val Val Gln
            35                  40                  45

Pro Ser Leu Arg Met Leu His Ala Asp Ala Gly Pro Ala Cys Tyr Val
        50                  55                  60

Leu Gly Arg Ser Ser Leu Asn Ala Arg Gly Leu Leu Val Val Pro Thr
65                  70                  75                  80

Arg Trp Leu Pro Gly His Val Cys Ala Phe Val Val Tyr Asn Leu Thr
                85                  90                  95

Gly Val Pro Val Thr Leu Glu Ala Gly Ala Lys Val Ala Gln Leu Leu
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Pro Leu Leu Val
145                 150                 155                 160

Phe Thr Asn Glu Phe Asp Ala Glu Ala Pro Pro Ser Glu Arg Gly Thr
                165                 170                 175

Gly Gly Phe Gly Ser Thr Gly Ile
                180

(2) INFORMATION FOR SEQ ID NO:15:

(i) SEQUENCE CHARACTERISTICS:
    (A) LENGTH: 180 amino acids
    (B) TYPE: amino acid
    (C) STRANDEDNESS: single
    (D) TOPOLOGY: linear (xi) SEQUENCE DESCRIPTION: SEQ ID NO:15:

His Arg Asp Ser Ala Glu Tyr His Ile Asp Val Pro Leu Thr Tyr Lys
1               5                   10                  15

His Ile Ile Asn Pro Lys Arg Gln Glu Asp Ala Gly Tyr Asp Ile Cys
            20                  25                  30

Val Pro Tyr Asn Leu Tyr Leu Lys Arg Asn Glu Phe Ile Lys Ile Val
            35                  40                  45

Leu Pro Ile Ile Arg Asp Trp Asp Leu Gln His Pro Ser Ile Ala Tyr
    50                  55                  60

Ile Phe Gly Arg Ser Ser Lys Ser Arg Ser Gly Ile Ile Val Cys Pro
65                  70                  75                  80

Thr Ala Trp Pro Ala Gly Glu His Cys Lys Phe Tyr Val Tyr Asn Leu
                85                  90                  95

Thr Gly Asp Asp Ile Arg Ile Lys Thr Gly Asp Arg Leu Ala Gln Val
                100                 105                 110

Leu Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Val Gln Trp Tyr Phe Thr Lys Thr Leu Asp
145                 150                 155                 160

Leu Ile Ala Thr Pro Ser Glu Arg Gly Thr Arg Gly Phe Gly Ser Thr
                165                 170                 175

Asp Lys Glu Thr
                180

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:16:

AAGAGACACC CGCCATTTCA CCCAGTAA                                28

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

GGTGTCTCTT CAGAGCAGG                                          19

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (xi) SEQUENCE DESCRIPTION: SEQ ID NO:18:

TTACTGGGTG CAATGGCGGG T                                           21

(2) INFORMATION FOR SEQ ID NO:19:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:19:

Pro Cys Ser Glu Glu Thr Pro Ala Xaa Ser Pro
1               5                   10

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:20:

Pro Cys Ser Glu Glu Thr Pro Ala Xaa Ser Pro Ser Lys Arg
1               5                   10